United States Patent
Schalkwijk et al.

(10) Patent No.: US 11,572,336 B2
(45) Date of Patent: Feb. 7, 2023

(54) PANTOTHENAMIDE ANALOGUES

(71) Applicant: MMV MEDICINES FOR MALARIA VENTURE, Geneva (CH)

(72) Inventors: Josephus Schalkwijk, Molenhoek (NL); Pedro Harold Han Hermkens, Oss (NL); Koen Jakob Dechering, Nijmegen (NL); Roger Victor Bonnert, Loughborough (GB)

(73) Assignee: MMV MEDICINES FOR MALARIA VENTURE, Geneva (CH)

( * ) Notice: Subject to any disclaimer, the term of this patent is extended or adjusted under 35 U.S.C. 154(b) by 0 days.

(21) Appl. No.: 17/418,871

(22) PCT Filed: Dec. 30, 2019

(86) PCT No.: PCT/EP2019/087147
§ 371 (c)(1),
(2) Date: Jun. 28, 2021

(87) PCT Pub. No.: WO2020/141155
PCT Pub. Date: Jul. 9, 2020

(65) Prior Publication Data
US 2022/0073450 A1     Mar. 10, 2022

(30) Foreign Application Priority Data
Dec. 31, 2018 (EP) ..................... 18215980

(51) Int. Cl.
C07C 235/10 (2006.01)
A61P 33/06 (2006.01)
A61K 45/06 (2006.01)
C07C 255/60 (2006.01)

(52) U.S. Cl.
CPC ............ *C07C 235/10* (2013.01); *A61K 45/06* (2013.01); *A61P 33/06* (2018.01); *C07C 255/60* (2013.01)

(58) Field of Classification Search
CPC .............................. C07C 235/10; A61P 33/06
See application file for complete search history.

(56) References Cited

U.S. PATENT DOCUMENTS

2018/0282317 A1  10/2018  Lin et al.

FOREIGN PATENT DOCUMENTS

| WO | WO 00/35298    | 6/2000  |
| WO | WO 2011/152720 | 12/2011 |
| WO | WO 2011/152721 | 12/2011 |
| WO | WO 2016/072854 | 5/2016  |

OTHER PUBLICATIONS

Forte, B. et al. "Prioritization of Molecular Targets for Antimalarial Drug Discovery" *ACS Infectious Diseases*, Sep. 15, 2021, pp. 2764-2776, vol. 7.
De Vries, L. E. et al. "Preclinical characterization and target validation of the antimalarial pantothenamide MMV693183" *Nature Communications*, 2022, pp. 1-16, vol. 13, No. 2158.
Awuah, E. et al. "Exploring structural motifs necessary for substrate binding in the active site of *Escherichia coli* pantothenate kinase" *Bioorg Med Chem.*, Jun. 15, 2014 pp. 1-20, vol. 22, No. 12.
Burello, E. et al. "Application of computer assisted combinatorial chemistry in antivirial, antimalarial and anticancer agents design" *Molecular Physics*, Oct. 10, 2002, pp. 3187-3198, vol. 100, No. 19.
Kirkman, L. A. et al. "Antimalarial proteasome inhibitor reveals collateral sensitivity from intersubunit interactions and fitness cost of resistance" *PNAS*, Jul. 2, 2018, pp. E6863-E6870, vol. 115, No. 29.
Written Opinion in International Application No. PCT/EP2019/087147, dated Mar. 9, 2020, pp. 1-14.
De Villiers, M. et al. "Structural Modification of Pantothenamides Counteracts Degradation by Pantetheinase and Improves Antiplasmodial Activity" *ACS Med. Chem. Lett.*, Jun. 17, 2013, pp. 784-789, vol. 4.
De Vries, L. E. et al. "Preclinical characterization and target validation of the antimalarial pantothenamide MMV693183" *bioRxiv*, May 14, 2021, pp. 1-35.
Eastman, R. T. et al. "Artemisinin-based combination therapies: a vital tool in efforts to eliminate malaria" *Nat Rev Microbiol.*, Dec. 2009, pp. 1-24, vol. 7, No. 12.
Howieson, V. M. et al. "Triazole Substitution of a Labile Amide Bond Stabilizes Pantothenamides and Improves Their Antiplasmodial Potency" *Antimicrobial Agents and Chemotherapy*, Dec. 2016 (accepted manuscript posted online Sep. 19, 2016), pp. 7146-7152, vol. 60, No. 12.
Jansen, P. A. M. et al. "Combination of Pantothenamides with Vanin Inhibitors as a Novel Antibiotic Strategy against Gram-Positive Bacteria" *Antimicrobial Agents and Chemotherapy*, Oct. 2013 (published ahead of print on Jul. 22, 2013), pp. 4794-4800, vol. 57, No. 10.
Macuamule, C. J. et al. "A Pantetheinase-Resistant Pantothenamide with Potent, On-Target, and Selective Antiplasmodial Activity" *Antimicrobial Agents and Chemotherapy*, Jun. 2015 (accepted manuscript posted online Apr. 6, 2015), pp. 3666-3668, vol. 59, No. 6.

(Continued)

*Primary Examiner* — Yong S. Chong
(74) *Attorney, Agent, or Firm* — Saliwanchik, Lloyd & Eisenschenk

(57) ABSTRACT

The present invention provides compounds that have antimalarial activity. More in particular, the present invention provides novel compounds that are analogues of pantothenamides. The pantothenamide analogues of this invention have particularly low $IC_{50}$ values against the asexual blood stages and gametocytes of malaria parasites. Furthermore, the pantothenamide analogues of this invention are characterized by low hepatic metabolism. Therefore, pantothenamide analogues of the invention are particularly suitable for use in therapeutic and/or prophylactic treatment of protozoan infections in a human or animal subject in need thereof. The invention further provides pharmaceutical formulations comprising the pantothenamide analogues as well as the therapeutic and/or prophylactic uses of the pantothenamide analogues and pharmaceutical formulations comprising them.

11 Claims, 1 Drawing Sheet

(56) References Cited

OTHER PUBLICATIONS

Schalkwijk, J. et al. "Antimalarial pantothenamide metabolites target acetyl—coenzyme A biosynthesis in *Plasmodium falciparum*" *Science Translational Medicine*, Sep. 18, 2019, pp. 1-15, vol. 11, eaas9917.
Spry, C. et al. "Coenzyme A biosynthesis: an antimicrobial drug target" *FEMS Microbiol Rev.*, 2008 (published online Dec. 2007), pp. 56-106, vol. 32.
Spry, C. et al. "Pantothenamides Are Potent, On-Target Inhibitors of *Plasmodium falciparum* Growth When Serum Pantetheinase Is Inactivated" *PLoS One*, Feb. 6, 2013, pp. 1-12, vol. 8, Issue 2, e54974.

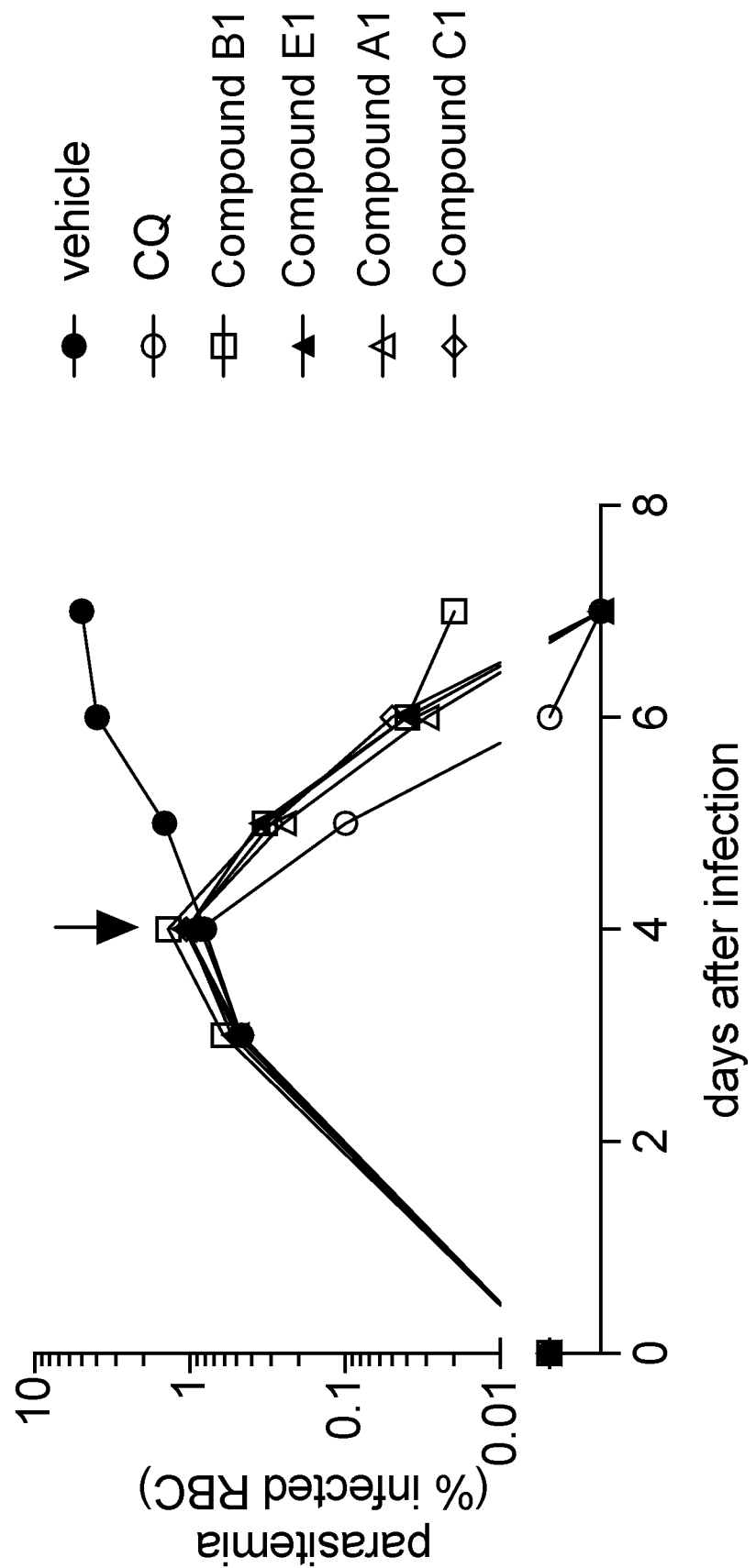

PANTOTHENAMIDE ANALOGUES

CROSS-REFERENCE TO RELATED APPLICATION

This application is the U.S. national stage application of International Patent Application No. PCT/EP2019/087147, filed Dec. 30, 2019.

FIELD OF THE INVENTION

The present invention concerns compounds and compositions having antimalarial activity. More in particular, the present invention provides novel analogues of pantothenamides that are potent inhibitors of (multiple stages of) the human malaria parasite and have excellent resistance against metabolic degradation. The use of these compounds and compositions in the therapeutic and/or prophylactic treatment of malaria in humans and animals is also provided.

BACKGROUND OF THE INVENTION

Malaria is one of the three major infectious diseases, reportedly causing about 200 million infections and more than four hundred thousand deaths per year in the world, mainly in developing countries in tropics. The disease is spread by mosquito species infected with any of four kinds of pathogens (plasmodia) causing malaria in humans, notably *P. falciparum, P. vivax, P. malariae* and *P. ovale*, all belonging to the phylum Apicomplexa. As there is currently no effective vaccine against malaria, control of this disease relies strongly on antimalarial chemotherapy. Increasing reports of antibiotic resistance against current antimalarial agents have emphasized the critical need for the development of antimalarial compounds with novel modes of action. Nevertheless, since the discovery of chloroquine in the late 40's of the previous century, only a few classes of new antimalarial drugs have been introduced (Eastman and Fidock, 2009, *Nature Rev Microbiol* 7:864-874). Shortly after the discovery and introduction of penicillin before World War II, as an antibiotic against bacteria, a multitude of potential antibiotics against bacteria, fungi and protozoan parasites have been synthesized. Many of these compounds were derivatives of natural metabolites, including vitamins, intended to investigate their potential use as antimetabolites.

In the early 70's already, amides derived from pantothenic acid have been reported to possess antibiotic activity in vitro. Later, derivatives of pantothenic acid have been synthesized and tested for their antibacterial, antifungal and antimalarial activity (Spry et al., 2008, *FEMS Microbiol Rev* 32:56-106). Pantothenate or pantothenic acid (vitamin B5) is required for CoA biosynthesis and is an essential and rate limiting nutrient for survival and/or growth of numerous bacteria, fungi and protozoa. A range of pantothenate analogues has been reported to possess activity against bacteria, fungi and malaria parasites (Spry et al. 2008, supra). In 1970, amides derived from pantothenic acid were first reported to possess antibacterial activity in vitro. Pantothenamides, of which N-pentylpantothenamide (N5-Pan) and N-heptylpantothenamide (N7-Pan) are the prototypes, are active against Gram-negative and Gram-positive bacteria. During the last few decades, many of these pantothenamides have been synthesized and the putative modes of action have been studied in detail.

Pantothenamides have been shown to serve as substrates or inhibitors (either competitive or allosteric) of pantothenate kinase (PanK), the first enzyme in the CoA biosynthesis pathway. Upon binding PanK-catalysed pantothenate phosphorylation may partially or completely be inhibited. In the case that pantothenamides serve as PanK substrates, competing with the natural substrate pantothenic acid, the resulting 4'-phosphopantothenamides may be further metabolized by the CoA biosynthetic machinery to yield analogues of CoA, as was shown for *E. coli* and *P. falciparum* malaria parasites (bioRxiv 256669). Such CoA analogues were found to be incorporated in acyl carrier protein, thereby inhibiting its function in bacterial fatty acid biosynthesis, which requires the 4'-phosphopantetheine moiety of CoA to be active. Whether the mechanisms that ultimately result in antimicrobial activity in the various target organisms (bacteria, fungi, protozoa) are the result of inhibition of CoA biosynthesis, fatty acid biosynthesis or another CoA-utilizing process, or a combination of the above, remains to be resolved.

In spite of their potential selectivity for bacterial, fungal and/or protozoan metabolic routes that has been known for decades, no pantothenamide compound has ever made it to the clinic. Spry et al., 2013, *Plos One* 8: e54974 studied the effect of a series of pantothenamides on the growth of erythrocytic stage *P. falciparum* parasites. They found that under standard in vitro culture conditions pantothenamides inhibit parasite growth, albeit with modest potency. They also describe that the antiplasmodial potency of pantothenamides was enhanced considerably when the parasite culture medium used for growth assays (which contained the commonly used serum substitute Albumax II or human serum) is pre-incubated at 37° C. for a prolonged period. Consequently, sub-micromolar concentrations of pantothenamides that have no effect in freshly prepared serum-containing medium inhibited parasite growth effectively in the pre-incubated medium. Spry et al. linked this finding to the presence in parasite culture medium of pantetheinase activity.

These findings are consistent with those described by Jansen et al. 2013, *Antimicrob Agents Chemother* 57:4794-4800. Jansen et al. have recently shown that pantothenamides are not active as antimicrobials in the presence of serum, and found that they were hydrolyzed by ubiquitous pantetheinases of the vanin family. To address this, a series of pantetheinase inhibitors based on a pantothenate scaffold were synthesized, which proved to inhibit serum pantetheinase activity in the nanomolar range. Mass spectrometric analysis showed that addition of these pantetheinase inhibitors prevented hydrolysis of pantothenamides by serum. Combinations of these novel pantetheinase inhibitors and prototypic pantothenamides like N5-Pan and N7-Pan exert antimicrobial activity in vitro, particularly against Gram-positive bacteria (*Staphylococcus aureus, Staphylococcus epidermidis, Streptococcus pneumoniae*, and *Streptococcus pyogenes*) even in the presence of serum. These results indicate that pantothenamides, when protected against degradation by host pantetheinases, are potentially useful antimicrobial agents. These findings have also been described in patent applications WO 2011/152720 and WO 2011/152721 for applications in bacterial and protozoal (malaria) infection.

Together these data are consistent with pantetheinase-mediated pantothenamide degradation occurring in serum, which forms the likely reason that pantothenamides had not made it to clinical practice, despite their promising activity (amongst others) as *plasmodium* inhibitors established in vitro.

In WO 2016072854, a new class of pantothenamide analogues was disclosed that is highly resistant to pantetheinase hydrolytic activity. These compounds have the characteristic feature that one of the amide bonds, i.e. the one not indigenous to pantothenic acid, is incorporated in reversed orientation. It was shown in WO 2016/6072854 that the compounds have sufficient stability in body fluids (i.e. ex vivo), while the antimicrobial activity is preserved. This was a significant step forward towards the actual clinical development of the pantothenamide analogues.

It is the object of the present invention to provide improved variants of pantothenamide analogues of the prior art, which combine i) resistance to pantetheinase hydrolytic activity, ii) high antimicrobial activity against protozoa, in particular against parasitic protozoans belonging to the *plasmodium* type such as *P. falciparum, P. vivax, P. ovale, P. malariae* or *P. knowlesi*, and iii) high resistance against metabolic degradation.

SUMMARY OF THE INVENTION

The present inventors have surprisingly found that the objectives of the invention are realized with the pantothenamide analogues described herein.

Compared to the prior art pantothenamide analogues and derivatives disclosed in WO2016072854, characteristic features of the analogues of this invention concern, in particular, the moieties flanking the inverted amide. The carbon atom flanking the inverted amide in the centre portion of the molecule comprises a methyl substituent. The two nitrogen atoms are separated by a linker of two carbon atoms. The moiety flanking the inverted amide at the distal portion of the molecule is a (hetero)aromatic, optionally substituted, ring or ring system, bonded directly to the carbonyl group of the inverted amide.

As will be illustrated in the examples provided herein, the pantothenamide analogues of this invention have particularly low $IC_{50}$ values against the asexual blood stages and gametocytes of malaria parasites. Particularly preferred pantothenamide analogues of the invention have $IC_{50}$ values of 10 nM or less, such as 5 nM or less, against asexual blood stages and/or gametocytes of *Plasmodium falciparum* parasites.

Furthermore, as will be illustrated in the examples provided herein, the pantothenamide analogues of this invention are characterized by low hepatic metabolism. Particularly preferred pantothenamide analogues of the invention have intrinsic clearance values of less than 2.5 µl/min/10$^6$ cells.

Examples provided herein describe the results of in vivo efficacy tests in a humanized mouse model for malaria infection. Improved in vivo efficacy of the pantothenamide analogues of the invention could be established, in keeping with the low $IC_{50}$ values, the resistance to pantetheinase hydrolytic activity and low hepatic metabolism as established in vitro.

The present invention thus provides new pantothenamide analogues that are particularly suitable for use in therapeutic and/or prophylactic treatment of protozoan infections, in particular infections of parasitic protozoans belonging to the *plasmodium* type such as *P. falciparum, P. vivax, P. ovale, P. malariae* or *P. knowlesi*, in a human or animal subject in need thereof. The invention further provides pharmaceutical formulations comprising the present pantothenamide analogues as well as the therapeutic and/or prophylactic uses of the pantothenamide analogues and pharmaceutical formulations comprising them.

These and other aspects of the invention, will become apparent to those of average skill in the art, based on the following description and examples.

DETAILED DESCRIPTION OF THE INVENTION

A first aspect of the present invention is directed to compounds selected from the group consisting of the pantothenamide analogues represented by formula (I):

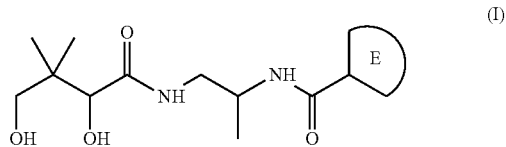 [SMILES: CC(CNC(=O)C(O)C(C)(C)CO)NC(=O)C(C)C]

wherein ring E represents an optionally substituted phenyl ring or a pharmaceutically acceptable salt thereof.

The compounds of the present invention are referred to herein as 'pantothenamide analogues'. This term is used because the compounds are (inverted amide) analogues of pantothenamide and derivatives thereof, as will be clear to those skilled in the art, based on the explanation and structural formula presented here above. The compounds of the invention are also referred to herein as 'antiprotozoal compound'. As indicated here above, the compounds of the invention are particularly effective against parasitic protozoans belonging to the *plasmodium* type such as *P. falciparum, P. vivax, P. ovale, P. malariae* or *P. knowlesi*, which are known to cause malaria.

The term "pharmaceutically acceptable salts" refers to salts of the compounds according to the invention. Examples of such salts are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, methane sulfonic acid, p-toluene sulfonic acid and poly-galacturonic acid.

In the context of the present invention are encompassed pharmaceutically acceptable salts, hydrates, solvates, or polymorphs of compounds of the invention.

In a particularly preferred embodiment, ring E represents phenyl, which phenyl may be unsubstituted or may be substituted with 1-3 substituents independently selected from nitril and halo, preferably selected from nitril, chloro and fluoro, preferably selected from nitril and fluoro, preferably fluoro.

In a particularly preferred embodiment, ring E represents a substituted phenyl, most preferably a phenyl ring substituted with 1, 2 or 3 substituents, independently selected from nitril and halo, preferably selected from nitril, chloro and fluoro, preferably selected from nitril and fluoro, preferably fluoro.

In a particularly preferred embodiment, ring E represents a substituted phenyl ring, most preferably a phenyl ring substituted with 1, 2 or 3 substituents, independently selected from, chloro and fluoro.

In a particularly preferred embodiment, ring E represents a substituted phenyl ring, most preferably a phenyl ring substituted with 1 nitril group.

In one particularly preferred embodiment, ring E represents a phenyl ring comprising an ortho fluoro group and one or two further substituents, preferably selected from fluoro, chloro and nitril, preferably from fluoro and nitril.

In one particularly preferred embodiment, ring E represents a phenyl ring comprising a meta fluoro group and optionally one or two further substituents, preferably selected from fluoro, chloro and nitril, preferably fluoro.

In one particularly preferred embodiment, ring E represents a phenyl ring comprising a meta nitril group and optionally one further substituent, preferably selected from fluoro and chloro, preferably fluoro.

In a particularly preferred embodiment, ring E represents a moiety selected from the group consisting of trifluoro-benzyl, difluoro-benzyl, fluoro-benzyl, fluoro-benzonitril, fluoro-chloro-benzyl and difluoro-chloro-benzyl.

In accordance with a preferred embodiment of the invention, pantothenamide analogues as defined herein are provided, which pantothenamide analogues are characterized by an $IC_{50}$ value against *P. falciparum* asexual blood stage parasites of less than 10 nM, preferably less than 8 nM, less than 7, less than 6 or less than 5 nM. The $IC_{50}$ value *P. falciparum* asexual blood stage parasites is determined according to the protocol defined in example 15 of this document.

In accordance with a preferred embodiment of the invention, pantothenamide analogues as defined herein are provided, which pantothenamide analogues are characterized by an intrinsic clearance ($Cl_{int}$) in a hepatocyte relay assay of less than 0.7 µl/min/$10^6$ cells, preferably less than 0.5, less than 0.4 or less than 0.3 µl/min/$10^6$ cells. The intrinsic clearance in a hepatocyte relay assay is determined according to the protocol defined in example 16 of this document.

In accordance with a preferred embodiment of the invention, pantothenamide analogues as defined herein are provided, which pantothenamide analogues are characterized by a half-life ($T_{1/2}$) in a hepatocyte relay assay of more than 2000 minutes, preferably more than 2500, more than 3'000 or more than 3'500 minutes. The half-life in a hepatocyte relay assay is determined according to the protocol defined in example 16 of this document.

In accordance with a preferred embodiment of the invention, pantothenamide analogues as defined herein are provided, which pantothenamide analogues are characterized by an in vivo efficacy in female NODscidIL2Rγnull mice infected with *P. falciparum* strain Pf3D70087/N9, said efficacy being expressed as the log reduction in parasitemia at 50 mg/kg p.o., of more than 2.0, preferably more than 2.4, more than 2.5, more than 2.6, more than 2.7, more than 2.8, more than 2.9 or more than 3.0. The in vivo efficacy as defined here, is determined according to the protocol described in example 17 of this document.

Preferred antiprotozoal compounds of the present invention include compounds (A) to (J) having the structures as shown in the Table 1.

TABLE 1

| No. | Structure |
| --- | --- |
| (A) | 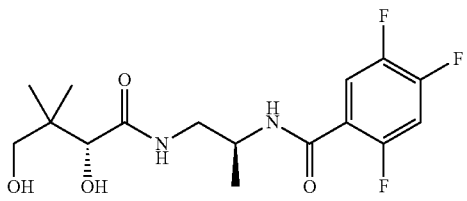 [SMILES: C[C@@H](CNC(=O)[C@H](O)C(C)(C)CO)NC(=O)c1cc(F)c(F)cc1F] |
| (A1) | 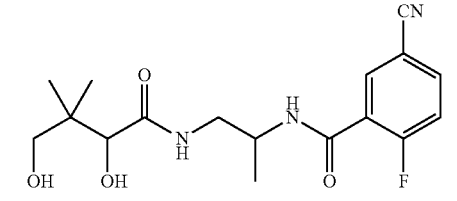 |
| (B) | 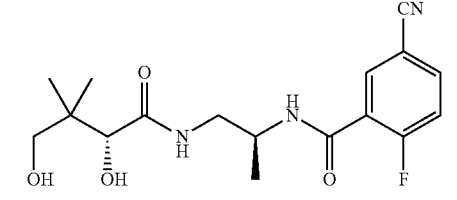 [SMILES: C[C@@H](CNC(=O)[C@H](O)C(C)(C)CO)NC(=O)c1cc(C#N)ccc1F] |
| (B1) | 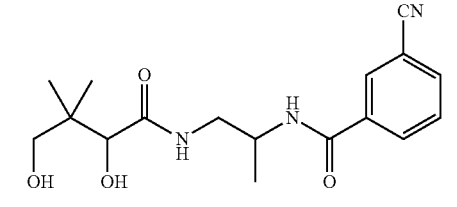 [SMILES: CC(CNC(=O)C(O)C(C)(C)CO)NC(=O)c1cccc(C#N)c1] |
| (C) | 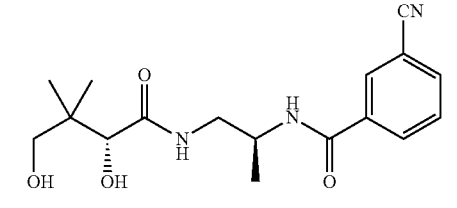 [SMILES: C[C@@H](CNC(=O)[C@H](O)C(C)(C)CO)NC(=O)c1cccc(C#N)c1] |
| (C1) | 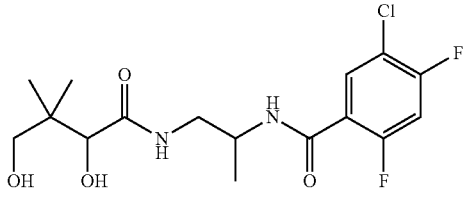 |
| (D) | 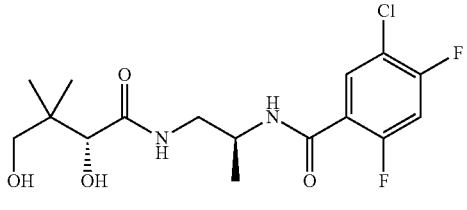 [SMILES: C[C@@H](CNC(=O)[C@H](O)C(C)(C)CO)NC(=O)c1cc(Cl)c(F)cc1F] |
| (D1) | 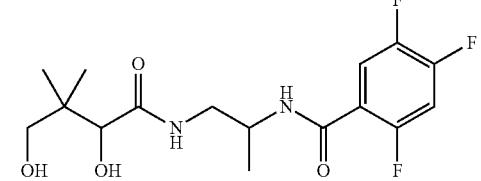 |

TABLE 1-continued

| No. | Structure |
|---|---|
| (E) | (structure: 3-fluorobenzamide derivative) |
| (E1) | (structure: 3-fluorobenzamide derivative, (2R,2S) stereochem) |
| (F) | (structure: 3-chlorobenzamide derivative) |
| (F1) | (structure: 3-chlorobenzamide derivative, (2R,2S) stereochem) |
| (G) | (structure: 3-chloro-4-fluorobenzamide derivative) |
| (G1) | (structure: 3-chloro-4-fluorobenzamide derivative, (2R,2S) stereochem) |
| (H) | (structure: 3,4-difluorobenzamide derivative) |
| (H1) | (structure: 3,4-difluorobenzamide derivative, (2R,2S) stereochem) |
| (I) | (structure: 5-chloro-2-fluorobenzamide derivative) |
| (I1) | (structure: 5-chloro-2-fluorobenzamide derivative, (2R,2S) stereochem) |
| (J) | (structure: 2,5-difluorobenzamide derivative) |
| (J1) | (structure: 2,5-difluorobenzamide derivative, (2R,2S) stereochem) |

Preferred antiprotozoal compounds of the present invention have the following IUPAC names (as generated using MarvinSketch version 16.8.15.0 (ChemAxon)):

A1: (2R)-2,4-dihydroxy-3,3-dimethyl-N-[(2S)-2-[(2,4,5-trifluorophenyl)formamido]propyl]butanamide B1: (2R)—N-[(2S)-2-[(5-cyano-2-fluorophenyl)formamido]propyl]-2,4-dihydroxy-3,3-dimethylbutanamide C1: (2R)—N-[(2S)-2-[(3-cyanophenyl)formamido]propyl]-2,4-dihydroxy-3,3-dimethyl butanamide D1: (2R)—N-[(2S)-2-[(5-chloro-2,4-difluorophenyl)formamido]propyl]-2,4-dihydroxy-3,3-dimethylbutanamide C1: (2R)—N-[(2S)-2-[(3-fluorophenyl)formamido]propyl]-2,4-dihydroxy-3,3-dimethylbutanamide F1: (2R)—N-[(2S)-2-[(3-chlorophenyl)formamido]propyl]-2,4-dihydroxy-3,3-dimethyl butanamide G1: (2R)—N-[(2S)-2-[(3-chloro-4-fluorophenyl)formamido]propyl]-2,4-dihydroxy-3,3-dimethyl butanamide H1: (2R)—N-[(2S)-2-[(3,4-difluorophenyl)formamido]propyl]-2,4-dihydroxy-3,3-dimethyl butanamide I1: (2R)—N-[(2S)-2-[(5-chloro-2-fluorophenyl)formamido]propyl]-2,4-dihydroxy-3,3-dimethyl butanamide J1: (2R)—N-[(2S)-2-[(2,5-difluorophenyl)formamido]propyl]-2,4-dihydroxy-3,3-dimethyl butanamide.

Particularly preferred antiprotozoal compounds include compounds (A), (B), (C) and (E) having the structures as shown in the Table 1.

In a most preferred embodiment, the antiprotozoal compound of the present invention is compound (A), having the structure as shown in the Table 1.

Preferred embodiments of the antiprotozoal compounds of the present invention include the compounds denominated (A1)-(J1) having the structures as shown in the Table 1.

Highly preferred antiprotozoal compounds include the compounds denominated (A1), (B1), (C1) and (E1) having the structures as shown in the Table 1.

In a most preferred embodiment, the antiprotozoal compound of the present invention is the compound denominated (A1), having the structure as shown in the Table 1.

Compounds of the invention contain at least two chiral centers and, therefore, exist as stereoisomers, such as enantiomers and diastereomers. According to the invention, the chemical structures depicted herein, and therefore the compounds of the invention, encompass all of the corresponding compound's stereoisomers, unless expressly indicated otherwise, for example by means of the Natta projection method. Thus, in accordance with the invention the chemical structures depicted herein by structural formula not indicating a specific stereochemistry, and therefore the compounds of the invention, encompass both a stereochemically pure form and mixtures of different stereoisomers, such as enantiomers and/or diastereomers. Thus, the invention encompasses compounds of Formula (I) in enantiomerically pure form, enantiomerically-enriched form, diastereomerically pure form, diastereomerically enriched form, as racemic mixture or as diastereomeric mixture.

In highly preferred embodiments, compounds of Formula I are provided wherein one of the stereoisomers makes up more than 60 mol %, more than 80 mol %, more than 90 mol %, more than 95 mol %, more than 97 mol %, more than 98.5 mol %, more than 99 mol % of the compound. In accordance with the invention, generally stated, a compound is considered stereochemically pure when one of the stereoisomers makes up more than more than 90 mol %, more than 95 mol %, more than 97 mol %, more than 98.5 mol %, more than 99 mol % of the compound.

Enantiomeric mixtures can be resolved into their component enantiomers or stereoisomers by well-known methods, such as chiral-phase gas chromatography, chiral-phase high performance liquid chromatography, or crystallizing the compound in a chiral solvent.

Diastereomeric mixtures can be resolved into their component diastereomers by well-known methods for separating two chemical compounds, for example based on their different melting points, boiling points etc.

Stereochemically pure compounds can also be obtained from stereochemically pure intermediates, reagents, and catalysts by well-known asymmetric synthetic methods.

In a particularly preferred embodiment of the invention, the pantothenamide analogues are 'stereochemically pure' (i.e. according to the above definition) derivatives or analogues of D(+)-pantothenamide, i.e. 'stereochemically pure' substances possessing the same stereochemical arrangement as the corresponding stereocenter in D(+)-pantothenamide.

When considering the antiprotozoal compound of the invention, two stereogenic centers a and b can be identified as follows:

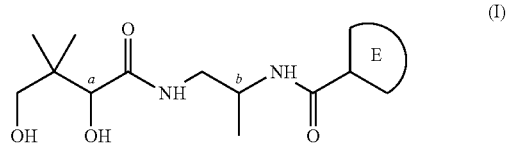 [SMILES: CC(CNC(=O)C(O)C(C)(C)CO)NC(=O)C(C)C]

In preferred embodiments in accordance with the invention an antiprotozoal compound as defined herein earlier is provided wherein the absolute configuration of stereogenic center a is R and/or the absolute configuration of stereogenic center b is S, preferably the absolute configuration of stereogenic center a is R and the absolute configuration of stereogenic center b is S. In highly preferred embodiments, the compound in accordance with the invention is stereochemically pure, as defined herein before, and the absolute configuration of stereogenic center a is R and the absolute configuration of stereogenic center b is S.

Also encompassed by the present invention are prodrugs of the compounds of formula (I). The term "prodrug" refers to compounds that are rapidly transformed in vivo to yield the parent compounds of the above formula, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

Furthermore, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. The compounds of the invention may be in the form of solvates such as hydrates. All forms are within the scope of the invention.

The compounds of the invention can be provided as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the present invention can efficiently be synthesized using a method comprising the step of reacting a 1,2-diaminopropane wherein one amino group has been protected with pantolactone under conditions resulting in the formation of the backbone of the pantothenamide analogues of the present invention.

Thus, the invention provides a method of producing a compound, the method comprising a) providing a protected 1,2-diaminopropane of formula (II),

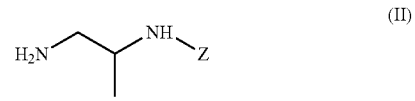

wherein Z represents an amine protecting group;
b) providing a pantolactone; and
c) reacting said 1, 2-diaminopropane with said pantolactone under conditions that result in the formation of a compound of formula (III)

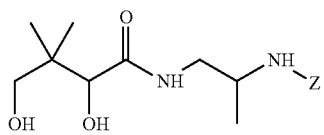

The reaction is illustrated in the below reaction scheme.

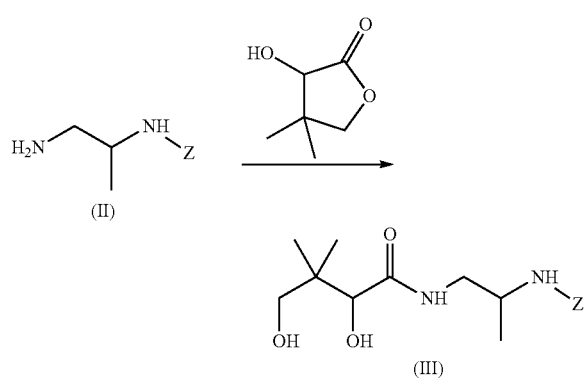

In preferred embodiments, the amine protecting group is selected from the group consisting of 9-fluorenylmethyl carbamate, t-butyl carbamate, benzyl carbamate, p-methoxybenzyl carbonyl, benzyl, 3,4-dimethoxybenzyl, preferably benzyl carbamate.

In highly preferred embodiments, more than 60 mol %, more than 80 mol %, more than 90 mol %, more than 95 mol %, more than 97 mol %, more than 98.5 mol %, more than 99 mol % of the compound of formula (II) provided in step a) is a single stereo-isomer, preferably the S-isomer.

In highly preferred embodiments, more than 60 mol %, more than 80 mol %, more than 90 mol %, more than 95 mol %, more than 97 mol %, more than 98.5 mol %, more than 99 mol % of the pantolactone provided in step b) is a single stereo-isomer, preferably D-(−)-pantolactone.

In preferred embodiments the reaction is performed in a solvent comprising an alcohol, such as methanol, ethanol or isopropanol, preferably ethanol.

In preferred embodiments the reaction is performed at a temperature above room temperature, preferably under reflux conditions.

In preferred embodiments the reaction is performed in the presence of a base, preferably a sterically hindered base, more preferably a sterically hindered amine base, such as triethylamine.

In embodiments the method further comprises the step d) reacting the compound of formula (III) to a compound of formula (I) as defined herein before.

Another aspect of the present invention concerns the compound of formula (III)

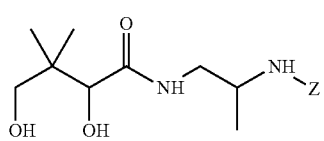

wherein Z represents an amine protecting group. In preferred embodiments Z is selected from the group consisting of 9-fluorenylmethyl carbamate, t-butyl carbamate, benzyl carbamate, p-methoxybenzyl carbonyl, benzyl, 3,4-dimethoxybenzyl, preferably benzyl carbamate. When considering the compound of formula (III), two stereogenic centers a and b can be identified as follows:

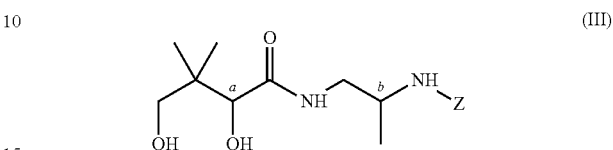

In preferred embodiments of the invention an antiprotozoal compound as defined herein earlier is provided wherein the absolute configuration of stereogenic center a is R and/or the absolute configuration of stereogenic center b is S, preferably the absolute configuration of stereogenic center a is R and the absolute configuration of stereogenic center b is S. In highly preferred embodiments, the compound in accordance with the invention is stereochemically pure, as defined herein before, and the absolute configuration of stereogenic center a is R and the absolute configuration of stereogenic center b is S.

Other aspects of the present invention concern:
- use of the pantothenamide analogues of the invention as defined herein before, as a medicament for treating a human or animal subject in need thereof,
- a method of therapeutic and/or prophylactic treatment of a human or animal subject in need thereof, said method comprising administering an effective amount of a pantothenamide analogue of the invention;
- a method for inactivating protozoan infection in a cell comprising the step of contacting the cell with an effective amount of at least one compound according to the invention and/or
- use of a pantothenamide analogue of the invention in the manufacture of a medicament for treating a human or animal subject in need thereof.

Typically, these methods and uses concern the treatment or prevention of a protozoal infection in a human or animal subject in need thereof, more preferably the treatment and/or prevention of infection by parasitic protozoans belonging to the plasmodium type. In embodiments the methods and uses provided herein concern the treatment or prevention of infection by one or more parasitic protozoans selected from the group consisting of P. falciparum, P. vivax, P. ovale, P. malariae and P. knowlesi, preferably selected from the group consisting of P. falciparum, P. vivax and P. ovale, preferably P. falciparum.

In another embodiment, the methods and uses as defined herein concern the prevention and/or treatment of disease caused by protozoa, more preferably the treatment and/or prevention of infection by parasitic protozoans belonging to the plasmodium type. In embodiments the methods and uses provided herein concern the prevention and/or treatment of disease caused by one or more parasitic protozoans selected from the group consisting of P. falciparum, P. vivax, P. ovale, P. malariae and P. knowlesi, preferably selected from the group consisting of P. falciparum, P. vivax and P. ovale, preferably P. falciparum.

In one embodiment, said disease is a disease selected from the group consisting of Malaria, Amoebiasis, Giardiasis, Toxoplasmosis, Cryptosporidiosis, Trichomoniasis, Chagas disease, Leishmaniasis, Sleeping Sickness, Dysentery, Acanthamoeba Keratitis, Primary Amoebic Meningoencephalitis, preferably malaria.

In a preferred embodiment of the invention, these uses and methods concern treatment of human subjects in need thereof, especially a subject infected by or at risk of becoming infected by protozoa as defined here above and/or a subject at risk of attracting a disease or condition as defined herein.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission. "Treatment" can also mean prolonging survival as compared to expected survival if not receiving treatment. The term "prevention" or "prophylaxis", or synonym thereto, as used herein refers to a reduction in the risk or probability of a patient attracting an infection or disease associated with infection.

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. In the context of disease, therapeutically effective amounts of the compounds of the present invention are used to treat, modulate, attenuate, reverse, or effect protozoal infection in a mammal. An "effective amount" is intended to mean that amount of a compound that is sufficient to treat, prevent or inhibit protozoal infections and/or diseases associated with such protozoal infections.

In certain embodiments, as described earlier, the disease or disorder associated with protozoal infections is malaria. Thus an effective amount is the amount sufficient to, when administered to the human or animal subject, prevent or inhibit malaria or a disease or a disorder associated with malaria or infection with a malaria parasite such as *P. falciparum, P. vivax, P. ovale, P. malariae* or *P. knowlesi*. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces malaria, e.g., as determined by clinical symptoms such as fever, anemia, and in severe cases, a coma potentially leading to death.

For administration to human patients, the total daily dose of the pantothenamide analogue of the invention is typically within the range 0.0001 mg/kg to 100 mg/kg body weight, preferably 0.001 mg/kg to 50 mg/kg body weight, more preferably 0.005 mg/kg to 25 mg/kg body weight, most preferably 0.01 mg/kg to 10 mg/kg body weight, the exact amount depending of course on the mode of administration and/or the severity of the disease or condition. For example, daily dosages for treatment by intravenous administration will typically be much lower than for oral treatment.

It is preferred that the pantothenamide analogues of the invention are administered repeatedly. Preferably, the compound is administered once, twice or three times daily to the patient. Embodiments are also envisaged wherein the compound of the present invention is administered less than once daily, e.g. once every two days, once every three days, once every four days or once a week. Even less frequent administration may be feasible using depot formulations.

Treatment may commence before, during or after exposure of the subject to a (potentially) infectious protozoan. The length of the treatment period depends on a variety of factors, such as the severity of the infection and/or disease, the age of the patient, the concentration and the activity of the pantothenamide analogue used. Typically, treatment lasts at least one day, more preferably at least two days, more preferably one week, more preferably at least two weeks, more preferably at least three weeks. As is generally known by those skilled in the art, repeated and continued administration typically reduces the risks of development of resistance towards the antiprotozoal and, without wishing to be bound by any particular theory, it is hypothesized that this might apply to compounds and combinations of the present invention.

It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

The pantothenamide analogues of the invention can be administered through any of the conventional routes. Oral administration may involve swallowing, so that the compound enters the gastrointestinal tract, or buccal or sublingual administration may be employed by which the compound enters the blood stream directly from the mouth. Parenteral administration may involve administration directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. The compounds of the invention may furthermore be administered transdermally, topically, intranasally or pulmonally. It is preferred that the pantothenamide analogues of the invention are administered orally, parenterally or topically, preferably orally or intravenously. Pantothenamide analogues of the invention may typically be administered to a human or animal subject as a pharmaceutical composition that is designed and optimized for a particular route of administration. Hence, another aspect of the invention concerns pharmaceutical compositions comprising pantothenamide analogue according to the invention.

Generally, the pantothenamide analogues will be administered as a formulation in association with one or more pharmaceutically acceptable excipients. The term "excipient" as used herein refers to any ingredient other than the pantothenamide analogue of the invention. The choice of excipient will, to a large extent, depend on factors such as the particular mode of administration, the effect of the excipient on solubility and stability, and the nature of the dosage form.

In a preferred embodiment of the invention a pharmaceutical composition for use in humans is provided comprising a pantothenamide analogue of the invention in a total amount within the range of 0.001 mg to 1000 mg, preferably 0.01 mg to 250 mg, more preferably 0.05 mg to 100 mg, most preferably 0.1 to 50 mg.

Compositions suitable for the delivery of the pantothenamide analogues of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Particularly suitable formulations for oral therapeutic administration, include tablets, buccal tablets, troches, capsules, elixirs, suspensions, syrups, wafers, and the like. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The pantothenamide analogues of the invention may also be incorporated in fast-dissolving, fast-disintegrating dosage forms such as those described in Expert Opinion in Therapeutic Patents, 1-1 (6), 981-986, by Liang and Chen (2001).

For tablet dosage forms, depending on dose, the pantothenamide analogue may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents. Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Various other materials may be present as coatings or to otherwise modify the physical form of the dosage unit. For instance, tablets may be coated with shellac, sugar or both. A syrup or elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations. The formulation of tablets is discussed in *Pharmaceutical Dosage Forms: Tablets, Vol.* 1, by H. Lieberman and L. Lachman (Marcel Dekker, New York, 1980). Suitable modified release formulations for the purposes of the invention are, such as high energy dispersions and osmotic and coated particles, are to be found in *Pharmaceutical Technology On-line,* 25(2), 1-14, by Verma et al. (2001). The use of chewing gum to achieve controlled release is described in WO 00/35298.

A pantothenamide analogue of the invention may also be administered parenterally. Solutions of a compound of the invention can be prepared in water suitably mixed with a surfactant such as hydroxypropylcellulose. Dispersions can also be prepared in glycerol, liquid polyethylene glycols, dimethylsulfoxide (DMSO) and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The pharmaceutical forms suitable for injectable use include aqueous solutions or dispersions as well as powders for the extemporaneous preparation of injectable solutions or dispersions. In all cases the form must be sterile. Furthermore the final injectable must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(lactic-co-glycolic acid) (PLGA) microspheres.

A pantothenamide analogue of the invention may also be administered topically, e.g. to the skin, the eye and/or mucosa. Hence, the pharmaceutical composition may be a suspension, solution, ointment, lotion, cream, foam, spray, balm or patch or occlusion bandage comprising a solution and/or suspension comprising the pantothenamide analogue, etc. Preferably however, the pharmaceutical composition may be selected from the group consisting of a lotion, an ointment, a gel, a cream and a spray. Solutions, creams, ointments or gels according to the present invention are semi-solid formulations that may be made by mixing the pantothenamide analogue, either as a finely divided or powdered form or in solution or suspension in an aqueous or non-aqueous fluid, with a greasy or non-greasy base, such as known to the person skilled in the art. Examples of bases are bases that may comprise one or more hydrocarbons such as hard, soft or liquid paraffin, glycerol, paraffin oil, beeswax, a metallic soap; a mucilage; an oil of natural origin such as almond, corn, arachis, castor or olive oil or derivatives thereof such as castor oil polyoxyl; wool fat or its derivatives or a fatty acid and/or ester such as steric or oleic acid, or isopropyl myristate. The base may furthermore comprise an alcohol such as propylene glycol, polyethylene glycol (PEG) of different molecular weights, cetyl alcohol, ethanol or a macrogel. The formulation may incorporate any suitable surface active agent or emulsifier such as an anionic, cationic or non-ionic surfactant such as a sorbitan ester, polysorbate, Cremophor® EL, Tween® 20, or a polyoxyethylene derivative thereof. Suspending agents such as natural gums, cellulose derivatives or inorganic materials such as siliceous silicas, and other ingredients such as lanolin, may also be included. An eye lotion may comprise a sterile aqueous solution and may be prepared by standard methods. Lotions or liniments for application to the skin may also include an agent to hasten drying and to cool the skin, such as an alcohol or acetone, and/or a moisturizer such as glycerol or an oil such as castor oil or arachis oil. In one preferred embodiment, the pharmaceutical formulations according to the present invention comprise one or more compounds selected from the group consisting of emulsifiers, hydroxy compounds and lipids, known to the person skilled in the art to be suitable for pharmaceutical formulations for topical administration. Preferably, the emulsifier is selected from the group consisting of Cremophor® EL, Tween® 20, polysorbate 80 and mixtures thereof, more preferably, the emulsifier is polysorbate 80. Preferably, the hydroxy compound is selected from the group consisting of ethanol, glycerol, propylene glycol, polyethylene glycol (PEG), cetyl alcohol and mixtures thereof. PEG-may be any molecular weight PEG, preferably however PEG 6000. Preferably, the lipid is selected from the group consisting of fatty alcohols, fatty acid esters, mineral oil, oil of natural origin and derivatives thereof and mixtures thereof. More preferably the lipid is selected from the group consisting of castor oil polyoxyl, paraffin oil and isopropyl myristate.

The pantothenamide analogues of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser.

As will be understood by those skilled in the art, the present invention provides compositions comprising combinations of two or more pantothenamide analogues of the invention.

The pantothenamide analogues of this invention can also be employed in conjunction with other active ingredients conventionally employed in the treatment of the conditions mentioned above. Such combined treatment may result in further enhancement of the efficacy of the treatment. Such further enhancement may be additive or even synergistic. Hence, the present invention provides compositions comprising pantothenamide analogues of the invention in combination with a further active ingredient, preferably a further antimalarial agent.

Examples of other active ingredients that can suitably be combined with the pantothenamide analogues of this invention include other antimalarial agents, such as atovaquone, chloroquine, hydroxychloroquine, primaquine, proguanil, quinidine, quinine, quinacrine, pyrimethamine-sulfadoxine, halofantrine, mefloquine, doxycycline, lumefantrine, amodiaquine, piperaquine, ferroquine, tafenoquine, arterolane, pyronaridine, artemisinin, artesunate, artemether, dihydroartemisinin, artenimol, spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)-(CAS Registry Number: 1193314-23-6), Sulfur, [4-[[2-(1,1-difluoroethyl)-5-methyl [1,2,4]triazolo[1,5-a]pyrimidin-7-yl]amino]phenyl]pentafluoro-] (CAS Registry Number: 1282041-94-4), Morpholine,4-[2-(4-cis-dispiro [cyclohexane-1,3'-[1,2,4]trioxolane-5',2''-tricyclo[3.3.1.1$^{3,7}$]decan]-4-ylphenoxy)ethyl]-(CAS Registry Number: 1029939-86-3), [3,3'-Bipyridin]-2-amine, 5-[4-(methylsulfonyl)phenyl]-6'-(trifluoromethyl)-(CAS Registry Number: 1314883-11-8), and Ethanone, 2-amino-1-[2-(4-fluorophenyl)-3-[(4-fluorophenyl)amino]-5,6-dihydroimidazo [1,2-a]pyrazin-7(8H)-yl]-(CAS Registry Number: 1261109-90-3). A further example of a compound for the treatment of malaria is the class of phenazines, especially riminophenazines, which have a substituted imino group in one benzene ring. In particular, N,5-bis-(phenyl)-3,5-dihydro-3-(cyclohexylimino)-2-phenazinamine has been reported to show antimalarial activity. As will be understood by those skilled in the art, combinations of a pantothenamide analogue of the invention and another antimalarial agent, is typically used in methods of treating and/or preventing malaria, and/or related conditions, typically by co-administration of the pantothenamide analogue and the additional antimalarial agent.

Another class of therapeutic agents which may suitably be used in conjunction with the pantothenamide analogues of the invention include the so-called resistance modifying agents. Resistance modifying agents may target and inhibit multiple drug resistance (MDR) mechanisms, rendering the parasites or bacteria susceptible to antimicrobials to which they were previously resistant. These compounds include among others efflux inhibitors and Beta Lactamase inhibitors.

As used herein, the terms "co-administration", "co-administered" and "in combination with", referring to the compounds of the invention and, optionally, the one or more other therapeutic agents, is intended to mean, and does refer to and include the following:
- simultaneous administration of such combination of compounds, when such components are formulated together into a single dosage form which releases said components at substantially the same time following administration,
- substantially simultaneous administration of such combination of compounds, when such components are formulated apart from each other into separate dosage forms which are administered at substantially the same time, where after said components are released at substantially the same time,
- sequential administration of such combination of compounds, when such components are formulated apart from each other into separate dosage forms which are administered at consecutive times with a significant time interval between each administration; and It is within the scope of the present invention that two or more pharmaceutical compositions, at least one of which contains a pantothenamide analogue in accordance with the invention, may conveniently be combined in the form of a kit suitable for co-administration of the compositions. Thus a kit of the invention typically comprises two or more separate pharmaceutical or veterinary composition, at least one of which contains a pantothenamide analogue in accordance with the invention as well as means for separately retaining said composition, such as a container, divided bottle, or divided foil packet. An example of such a kit is the familiar blister pack used for the packaging of tablets, capsules and the like.

The details and preferred embodiments of these aspects of the invention will be readily understood by those skilled in the art based on the foregoing detailed descriptions of the pantothenamide analogues, the compositions comprising them, the uses thereof and their methods of production. It will be recognized that these embodiments are susceptible to various modifications and alternative forms well known to those of skill in the art.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way

DESCRIPTION OF THE FIGURES

FIG. 1. In vivo efficacy of pantothenamide analogues A1, B1, C1 and E1. In the graph the parasitemia (% infected red blood cells (RBC)) is plotted agains the number of days after infection. The arrow indicates the moment of administration of the respective treatments (vehicle comprising one of the respective pantothenamide analogues, vehicle without patothenamide analogue and chloroquine treatment).

EXAMPLES

General Procedure for Amidation (General Procedure A)

To a stirred solution of Amine (A1) (1 eqv) and Acid (A2) (1.2 eqv) in tetrahydrofuran (THF) (5 ml/mmol) were added 1-[Bis(dimethylamino)methylene]-1H-1,2,3-triazolo[4,5-b] pyridinium 3-oxide hexafluorophosphate (HATU) (1.5 eqv) and triethylamine (Et$_3$N) (5 eqv) at 0° C. Reaction mixture was stirred at room temperature for 16 h. Reaction mixture was quenched with satd. sodium bicarbonate (NaHCO$_3$) solution and extracted with ethyl acetate (EtOAc). The organic layer was washed with water, brine, dried over sodium sulfate (Na$_2$SO$_4$) and concentrated under reduced pressure. Crude was purified over a preparative thin layer chromatography (prep TLC) plate (methanol (MeOH)-dichloromethane (DCM)) to afford desired amide (A3).

General Procedure for Acetonide Deprotection (General Procedure B)

To a stirred solution of amide (A3) (1 eqv) in acetonitrile (CH$_3$CN) (5 ml/mmol) was treated with bismuth(III)chloride (Bi(III)Cl$_3$) (0.1 eqv) and H$_2$O (0.04 ml/mmol). The reaction mixture was stirred at room temperature for 16 h. Reaction mass was concentrated under reduced pressure and purified over prep TLC (MeOH in DCM) to afford Final compound.

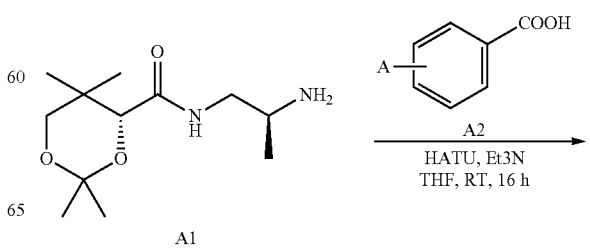

Example 1: synthesis of (2R)-2,4-dihydroxy-3,3-dimethyl-N-[(2S)-2-[(2,4,5-trifluorophenyl)-formamido]propyl]butanamide (A1)
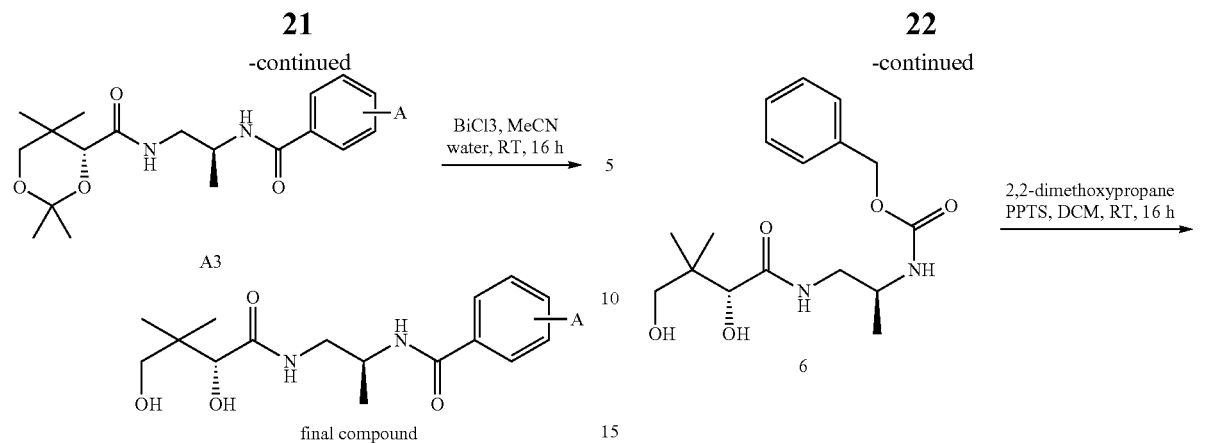

Synthesis of [(S)-2-(1,3-Dioxo-1,3-dihydro-isoindol-2-yl)-1-methyl-ethyl]-carbamic acid benzyl ester (3)

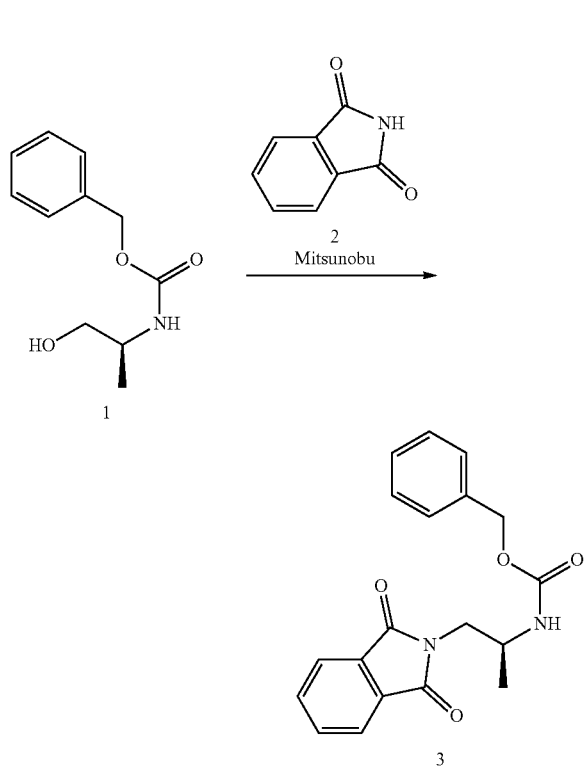

Procedure: To a stirred solution of ((S)-2-Hydroxy-1-methyl-ethyl)-carbamic acid benzyl ester (1) (50 g, 238.9 mmol) in dry THF (1500 mL) were added Phthalimide (2) (38.6 g, 262.8 mmol) and triphenylphosphine (PPh₃) (68.9 g 262.8 mmol). Then diethylazodicarboxylate (DEAD) (41.2 mL, 262.8 mmol) was added drop wise at 0° C. Reaction was stirred at room temperature (RT) for 16 h. The reaction mixture was then concentrated and the residue was purified by column chromatography (silica gel, 100-200 mesh) using 20% EtOAc in hexane to afford [(S)-2-(1,3-Dioxo-1,3-dihydro-isoindol-2-yl)-1-methyl-ethyl]-carbamic acid benzyl ester (3) (53 g, 65.5%) as off white solid.

Synthesis of ((S)-2-Amino-1-methyl-ethyl)-carbamic acid benzyl ester (4)

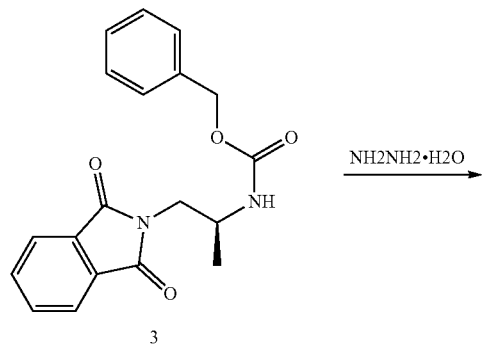

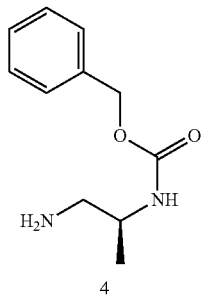

Procedure: To a stirred solution of [(S)-2-(1,3-Dioxo-1,3-dihydro-isoindol-2-yl)-1-methyl-ethyl]-carbamic acid benzyl ester (3) (53 g, 47.7 mmol) in ethanol (EtOH) (450 mL) was added hydrazine hydrate (116.8 mL, 2406.4 mmol). Reaction mass was heated at 50° C. for 2 h. Reaction mass was cooled to RT, filtered and concentrated under reduced pressure. The resulting residue was again suspended in Et2O and filtered. The combined filtrates were concentrated under reduced pressure to afford ((S)-2-Amino-1-methyl-ethyl)-carbamic acid benzyl ester (4) (30 g, 96%) as colorless sticky gum.

Synthesis of [(S)-2-((R)-2,4-Dihydroxy-3,3-dimethyl-butyrylamino)-1-methyl-ethyl]-carbamic acid benzyl ester (6)

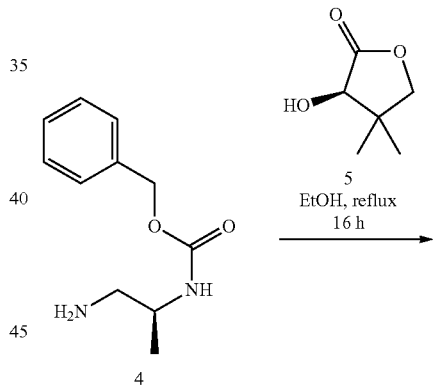

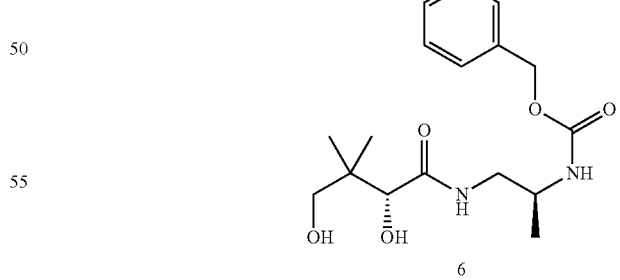

Procedure: To a stirred solution of ((S)-2-Amino-1-methyl-ethyl)-carbamic acid benzyl ester (4) (26 g, 124.8 mmol) in EtOH (150 mL) were added D-(−)-Pantolactone (5) (48.7 g, 374.5 mmol) and Et3N (60.9 mL, 436.9 mmol). Reaction mixture was refluxed for 16 h. Reaction mixture was concentrated under reduced pressure to get crude mass which was purified by column chromatography (silica gel, 100-200 mesh) using 3% MeOH in DCM to afford [(S)-2-((R)-2,4-Dihydroxy-3,3-dimethyl-butyrylamino)-1-methyl-ethyl]-carbamic acid benzyl ester (6) (31.2 g, 74%) as colorless sticky gum.

Synthesis of {(S)-1-Methyl-2-[((R)-2,2,5,5-tetramethyl-[1,3]dioxane-4-carbonyl)-amino]-ethyl}-carbamic acid benzyl ester (7)

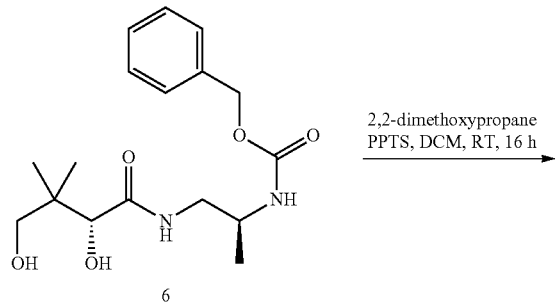

Procedure: To a stirred solution of [(S)-2-((R)-2,4-Dihydroxy-3,3-dimethyl-butyrylamino)-1-methyl-ethyl]-carbamic acid benzyl ester (6) (31.2 g, 92.2 mmol) in DCM (270 mL) were added pyrdinium-p-toluenesulfonate (9.2 g, 36.2 mmol) and 2,2-dimethoxypropane (113.3 g, 922 mmol). Reaction mixture was stirred at RT for 16 h. Solvent was removed under reduced pressure and the crude product was purified by column chromatography (silica gel, 100-200 mesh) using 1% MeOH in DCM to afford {(S)-1-Methyl-2-[((R)-2,2,5,5-tetramethyl-[1,3]dioxane-4-carbonyl)-amino]-ethyl}-carbamic acid benzyl ester (7) (22 g, 63%) as colorless sticky gum.

Synthesis of (R)-2,2,5,5-Tetramethyl-[1,3]dioxane-4-carboxylic acid ((S)-2-amino-propyl)-amide (8)

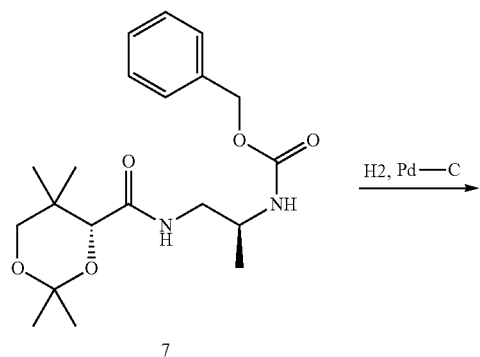

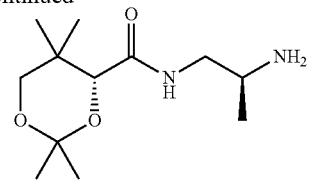

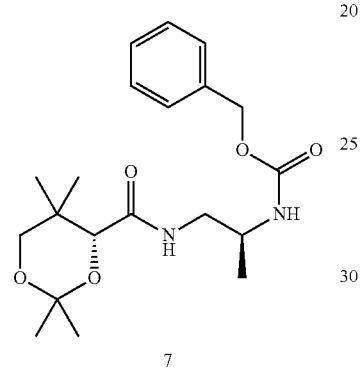

Procedure: To a stirred solution of {(S)-1-Methyl-2-[((R)-2,2,5,5-tetramethyl-[1,3]dioxane-4-carbonyl)-amino]-ethyl}-carbamic acid benzyl ester (7) (22 g, 58.1 mmol) in MeOH (160 mL) was degassed with nitrogen gas for 10 mins then 10% Pd/C (3 g) was added. Reaction mass was stirred at RT under hydrogen atmosphere (balloon pressure) for 3 h. Reaction mixture was filtered through celite and the filtrate was concentrated under reduced pressure to afford (R)-2,2,5,5-Tetramethyl-[1,3]dioxane-4-carboxylic acid ((S)-2-amino-propyl)-amide (8) (14 g, 98.5%) as colorless sticky gum.

Synthesis of (R)-2,2,5,5-Tetramethyl-[1,3]dioxane-4-carboxylic acid [(S)-2-(2,4,5-trifluoro-benzoylamino)-propyl]-amide (10)

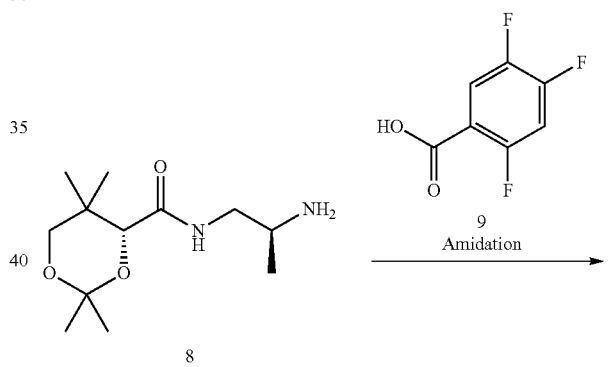

Procedure: Same as general procedure A with (R)-2,2,5,5-Tetramethyl-[1,3]dioxane-4-carboxylic acid ((S)-2-amino-propyl)-amide (8) (5 g, 20.492 mmol) and 2,4,5-Trifluoro-benzoic acid (9) (3.609 g, 20.492 mmol) to afford (R)-2,2,5,5-Tetramethyl-[1,3]dioxane-4-carboxylic acid [(S)-2-(2,4,5-trifluoro-benzoylamino)-propyl]-amide (10) as gum in 60.63% yield, 5 g.

27

Synthesis of (2R)-2,4-dihydroxy-3,3-dimethyl-N-[(2S)-2-[(2,4,5-trifluorophenyl) formamido]-propyl] butanamide (A1)

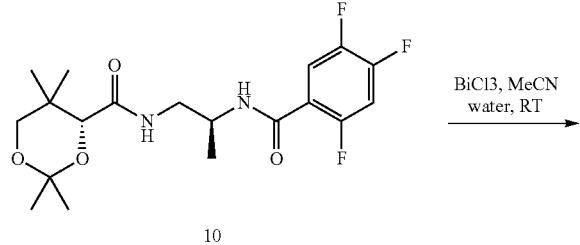

Procedure: Same as general procedure B with (R)-2,2,5,5-Tetramethyl-[1,3]dioxane-4-carboxylic acid [(S)-2-(2,4,5-trifluoro-benzoylamino)-propyl]-amide (10) (5 g, 12.425 mmol) to afford (2R)-2,4-dihydroxy-3,3-dimethyl-N-[(2S)-2-[(2,4,5-trifluorophenyl) formamido]propyl]-butanamide (A1) as light yellow sticky solid in 77.74% yield, 3.5 g. $^1$H NMR (400 MHz, DMSO-d$_6$) δ 8.24 (d, J=7.56 Hz, 1H), 7.84 (t, J=5.88 Hz, 1H), 7.72-7.63 (m, 2H), 5.41 (d, J=5.48 Hz, 1H), 4.44 (t, J=5.58 Hz, 1H), 4.07-4.03 (m, 1H), 3.73 (d, J=5.48 Hz, 1H), 3.32-3.24 (m, 2H), 3.19-3.12 (m, 2H), 1.10 (d, J=6.64 Hz, 3H), 0.77 (s, 3H), 0.76 (s, 3H). LCMS (HCOOH:ACN): M+H=363, R$_t$=1.46 min in 3 mins run.

Example 2: Synthesis of (2R)—N-[(2S)-2-[(5-cyano-2-fluorophenyl)formamido]propyl]-2,4-dihydroxy-3,3-dimethylbutanamide (B1)

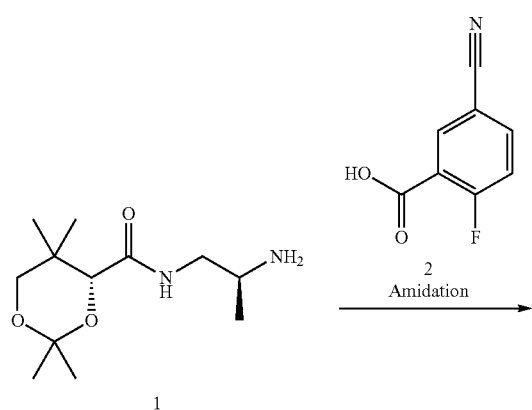

28

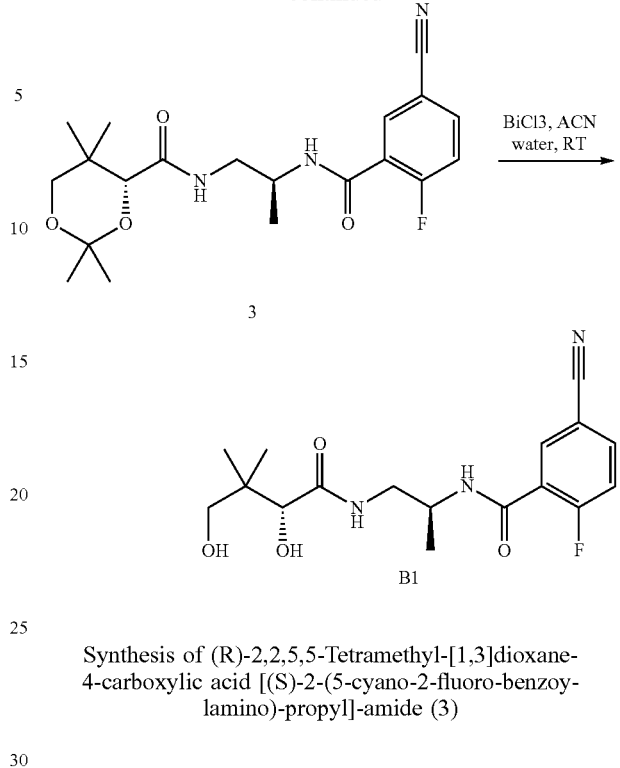

Synthesis of (R)-2,2,5,5-Tetramethyl-[1,3]dioxane-4-carboxylic acid [(S)-2-(5-cyano-2-fluoro-benzoylamino)-propyl]-amide (3)

Procedure: Same as general procedure A with (R)-2,2,5,5-Tetramethyl-[1,3]dioxane-4-carboxylic acid ((S)-2-amino-propyl)-amide (1) (4 g, 16.393 mmol) and 5-Cyano-2-fluoro-benzoic acid (2) (2.707 g, 16.393 mmol) to afford (R)-2,2,5,5-Tetramethyl-[1,3]dioxane-4-carboxylic acid [(S)-2-(5-cyano-2-fluoro-benzoylamino)-propyl]-amide (3) as gum in 56.57% yield, 3.63 g.

Synthesis of (2R)—N-[(2S)-2-[(5-cyano-2-fluoro-phenyl)formamido]propyl]-2,4-dihydroxy-3,3-dimethylbutanamide (B1)

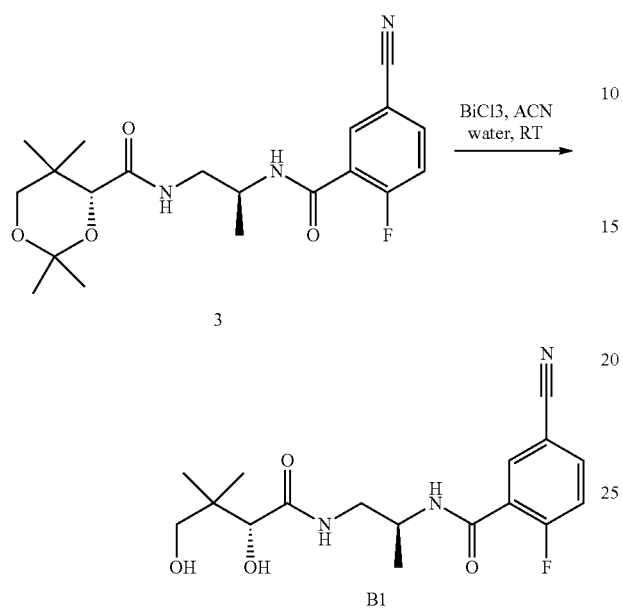

Procedure: Same as general procedure B with (R)-2,2,5,5-Tetramethyl-[1,3]dioxane-4-carboxylic acid [(S)-2-(5-cyano-2-fluoro-benzoylamino)-propyl]-amide (3) (3.63 g, 9.273 mmol) to afford (2R)—N-[(2S)-2-[(5-cyano-2-fluoro-phenyl)formamido]propyl]-2,4-dihydroxy-3,3-dimethyl-butanamide (B1) as off white sticky solid in 73.66% yield, 2.4 g. $^1$H NMR (400 MHz, DMSO-$d_6$) δ 8.39 (d, J=7.8 Hz, 1H), 8.08-8.02 (m, 2H), 7.84 (t, J=5.96 Hz, 1H), 7.54 (t, J=9.24 Hz, 1H), 5.41 (d, J=5.52 Hz, 1H), 4.45 (t, J=5.58 Hz, 1H), 4.08-4.02 (m, 1H), 3.74 (d, J=5.56 Hz, 1H), 3.31-3.23 (m, 2H), 3.20 (m, 2H), 1.10 (d, J=6.64 Hz, 3H), 0.78 (s, 3H), 0.77 (s, 3H). LCMS (HCOOH:ACN): M+H=352, $R_t$=1.35 min in 3 mins run.

Example 3: synthesis of (2R)—N-[(2S)-2-[(3-cyanophenyl)formamido]propyl]-2,4-dihydroxy-3,3-dimethylbutanamide (C1)

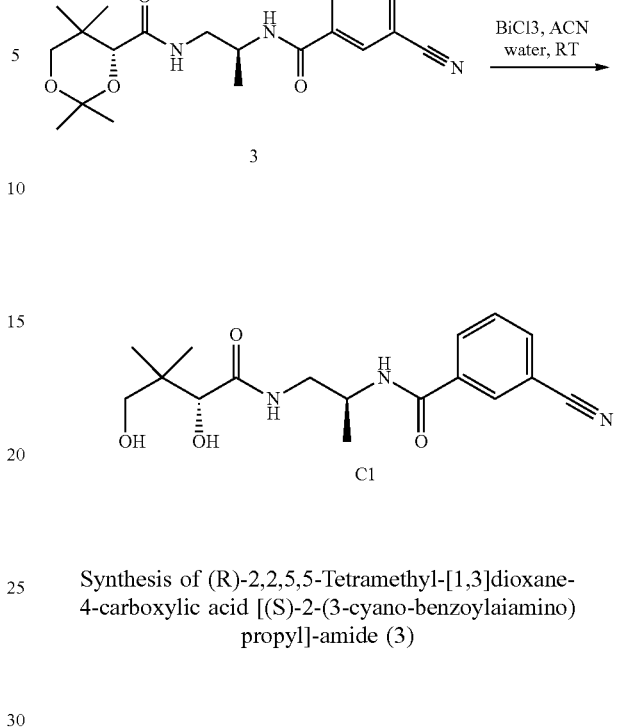

Synthesis of (R)-2,2,5,5-Tetramethyl-[1,3]dioxane-4-carboxylic acid [(S)-2-(3-cyano-benzoylaiamino)propyl]-amide (3)

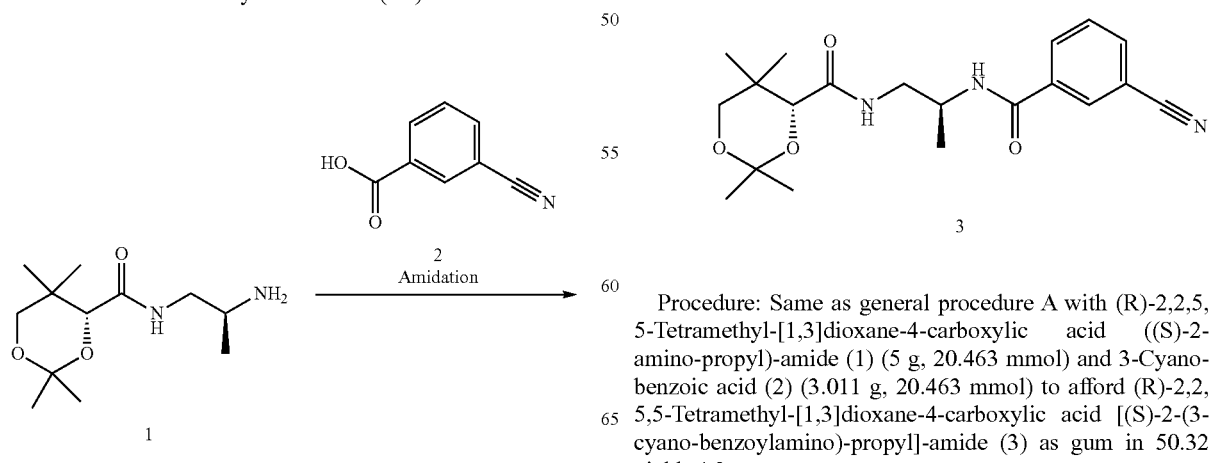

Procedure: Same as general procedure A with (R)-2,2,5,5-Tetramethyl-[1,3]dioxane-4-carboxylic acid ((S)-2-amino-propyl)-amide (1) (5 g, 20.463 mmol) and 3-Cyano-benzoic acid (2) (3.011 g, 20.463 mmol) to afford (R)-2,2,5,5-Tetramethyl-[1,3]dioxane-4-carboxylic acid [(S)-2-(3-cyano-benzoylamino)-propyl]-amide (3) as gum in 50.32 yield, 4.2 g.

Synthesis of (2R)—N-[(2S)-2-[(3-cyanophenyl) formamido]propyl]-2,4-dihydroxy-3,3-dimethyl-butanamide (C1)

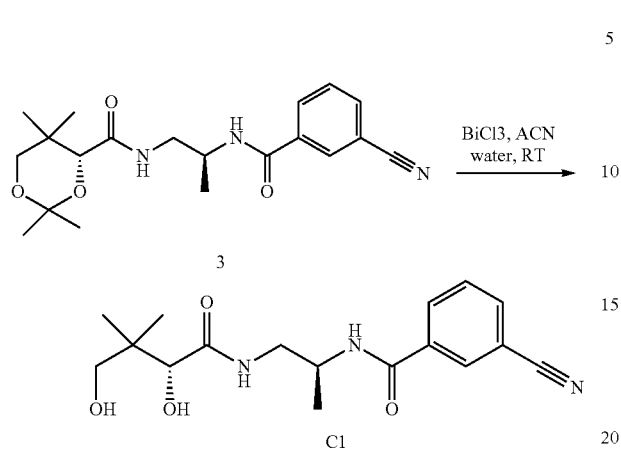

Procedure: Same as general procedure B with (R)-2,2,5,5-Tetramethyl-[1,3]dioxane-4-carboxylic acid ((S)-2-(3-cyano-benzoylamino)-propyl-amide (3) (4.2 g, 11.246 mmol) to afford (2R)—N-[(2S)-2-[(3-cyanophenyl)formamido]propyl]-2,4-dihydroxy-3,3-dimethylbutanamide (C1) as off white solid in 82.68 (yield, 3.1 g. $^1$H NMR (400 MHz, DMSO-$d_6$) δ 8.42 (d, J=7.6 Hz, 1H), 8.23 (s, 1H), 8.12 (d, J=6.64 Hz, 1H), 7.99 (d, J=7.44 Hz, 1H), 7.85 (brs, 1H), 7.68 (t, J=7.64 Hz, 1H), 5.39 (d, J=5.6 Hz, 1H), 4.43 (brs, 1H), 4.13-4.10 (m, 1H), 3.73 (d, J=5.6 Hz, 1H), 3.31-3.12 (m, 4H), 1.12 (d, J=6.36 Hz, 3H), 0.74 (s, 3H), 0.72 (s, 3H). LCMS (HCOOH:ACN): M+H=334, $R_t$=1.42 min in 3 mins run.

Example 4: Synthesis of (2R)—N-[(?2S)-2-[(5-chloro-2,4-difluorophenyl) formamido]propyl]-2,4-dihydroxy-3,3-dimethylbutanamide (D1)

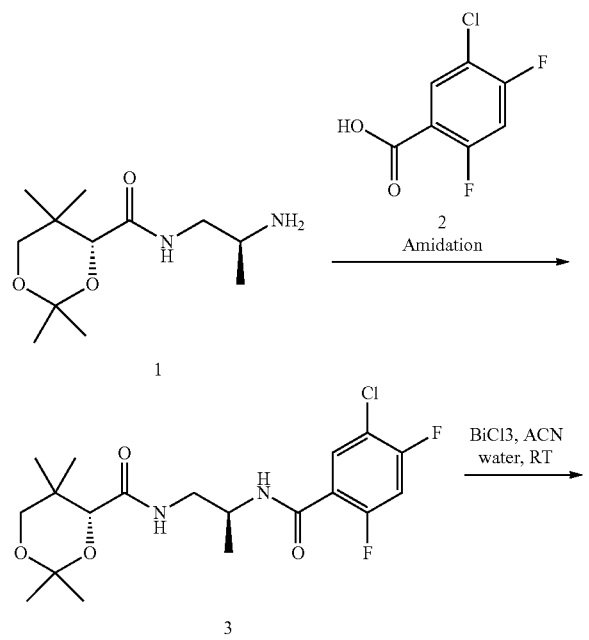

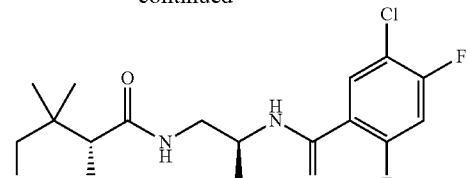

Synthesis of (R)-2,2,5,5-Tetramethyl-[1,3]dioxane-4-carboxylic acid [(S)-2-(5-chloro-2,4-difluoro-benzoylamino)-propyl]-amide (3)

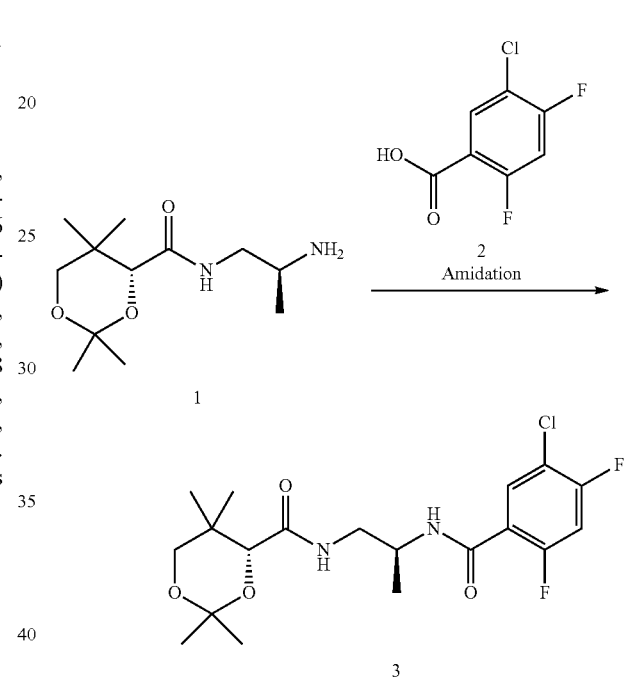

Procedure: Same as general procedure A with (R)-2,2,5,5-Tetramethyl-[1,3]dioxane-4-carboxylic acid ((S)-2-amino-propyl)-amide (1) (2.3 g, 9.413 mmol) and 5-Chloro-2,4-difluoro-benzoic acid (2) (2.175 g, 11.296 mmol) to afford (R)-2,2,5,5-Tetramethyl-[1,3]dioxane-4-carboxylic acid [(S)-2-(5-chloro-2,4-difluoro-benzoylamino)-propyl]-amide (3) as gum in 91.31% yield, 3.6 g.

Synthesis of (2R)—N-[(2S)-2-[(5-chloro-2,4-difluorophenyl)formamido]propyl]-2,4-dihydroxy-3,3-dimethylbutanamide (D1)

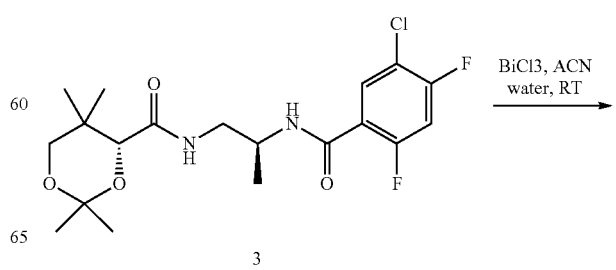

-continued

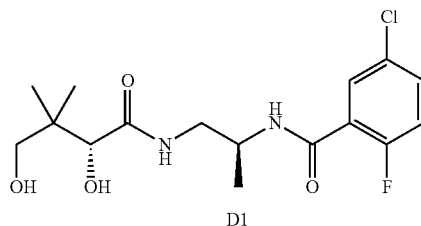

D1

Procedure: Same as general procedure B with (R)-2,2,5, 5-Tetramethyl-[1,3]dioxane-4-carboxylic acid [(S)-2-(5-chloro-2,4-difluoro-benzoylamino)-propyl]-amide (3) (3.2 g, 7.64 mmol) to afford (2R)—N-[(2S)-2-[(5-chloro-2,4-difluorophenyl)formamido]propyl]-2,4-dihydroxy-3,3-dimethylbutanamide (D1) as off white solid in 69.11% yield, 2 g. $^1$H NMR (400 MHz, DMSO-d$_6$) δ 8.28 (d, J=7.56 Hz, 1H), 7.85-7.80 (m, 2H), 7.65 (t, J=9.78 Hz, 1H), 5.41 (d, J=5.52 Hz, 1H), 4.44 (t, J=5.56 Hz, 1H), 4.08-4.01 (m, 1H), 3.73 (d, J=5.52 Hz, 1H), 3.31-3.24 (m, 2H), 3.19-3.13 (m, 2H), 1.10 (d, J=6.64 Hz, 3H), 0.77 (s, 3H), 0.76 (s, 3H). LCMS (HCOOH:ACN): M+H=379, R$_t$=1.43 min in 3 mins run.

Example 5: Synthesis of (2R)—N-[(2S)-2-[(3-fluorophenyl)formamido]propyl]-2,4-dihydroxy-3,3-dimethylbutanamide (E1)

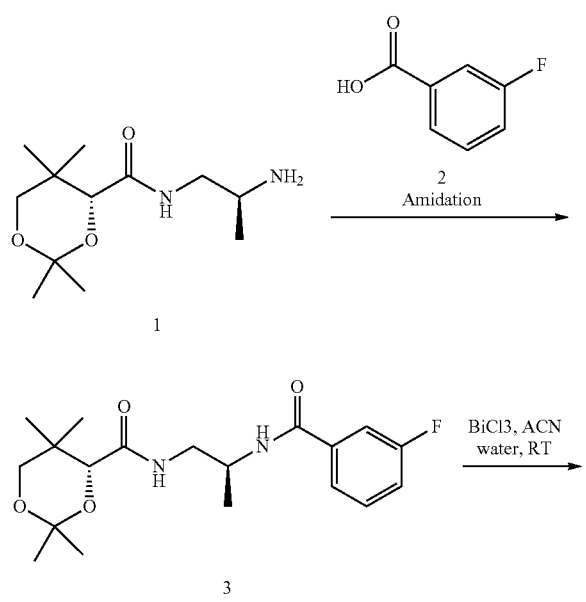

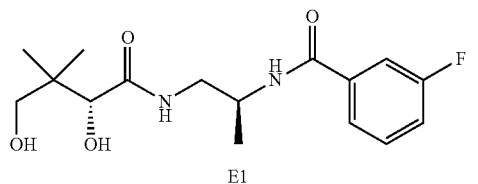

E1

Synthesis of (R)-2,2,5,5-Tetramethyl-[1,3]dioxane-4-carboxylic acid [(S)-2-(3-fluoro-benzoylamino)-propyl]-amide (3)

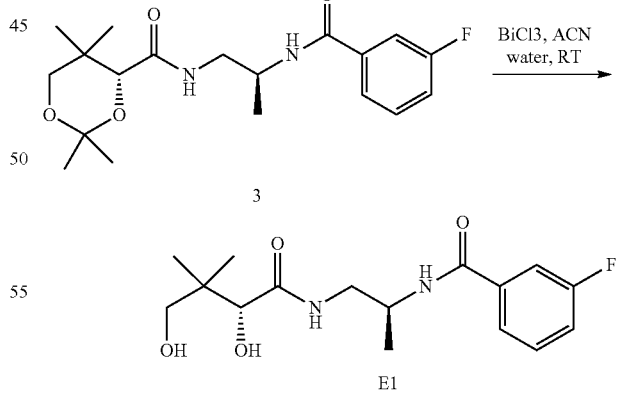

Procedure: Same as general procedure A with (R)-2,2,5,5-Tetramethyl-[1,3]dioxane-4-carboxylic acid ((S)-2-amino-propyl)-amide (1) (3 g, 12.295 mmol) and 3-Fluoro-benzoic acid (2) (1.723 g, 12.295 mmol) to afford (R)-2,2,5,5-Tetramethyl-[1,3]dioxane-4-carboxylic acid [(S)-2-(3-fluoro-benzoylamino)-propyl]-amide (3) as gum in 77.69% yield, 3.5 g.

Synthesis of (2R)—N-[(2S)-2-[(3-fluorophenyl)formamido]propyl]-2,4-dihydroxy-3,3-dimethylbutanamide (E1)

Procedure: Same as general procedure B with (R)-2,2,5,5-Tetramethyl-[1,3]dioxane-4-carboxylic acid [(S)-2-(3-fluoro-benzoylamino)-propyl]-amide (3) (3.5 g, 9.552 mmol) to afford (2R)—N-[(2S)-2-[(3-fluorophenyl)formamido]propyl]-2,4-dihydroxy-3,3-dimethylbutanamide (E1) as off white solid in 63.56% yield, 2.2 g. $^1$H NMR (400 MHz, DMSO-d$_6$) δ 8.31 (d, J=7.64 Hz, 1H), 7.85 (t, J=5.88

Hz, 1H), 7.66 (d, J=7.72 Hz, 1H), 7.61-7.58 (m, 1H), 7.53-7.48 (m, 1H), 7.39-7.34 (m, 1H), 5.40 (d, J=5.28 Hz, 1H), 4.44 (brs, 1H), 4.12-4.08 (m, 1H), 3.73 (d, J=5.28 Hz, 1H), 3.32-3.12 (m, 4H), 1.11 (d, J=6.64 Hz, 3H), 0.74 (s, 3H), 0.73 (s, 3H). LCMS (HCOOH:ACN). M+H=327, R$_t$=1.45 min in 3 mins run.

Example 6: Synthesis of (2R)—N-[(2S)-2-[(3-chlorophenyl)formamido]propyl]-2,4-dihydroxy-3,3-dimethylbutanamide (F1)

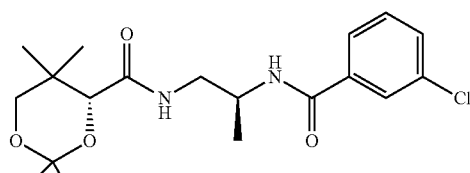

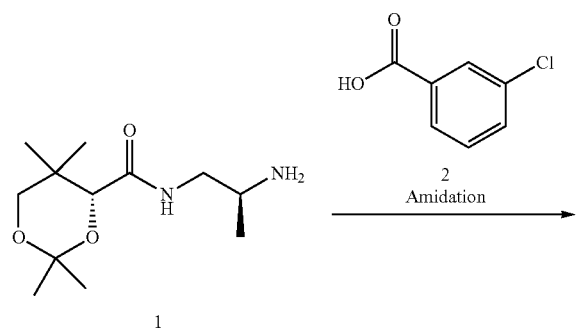

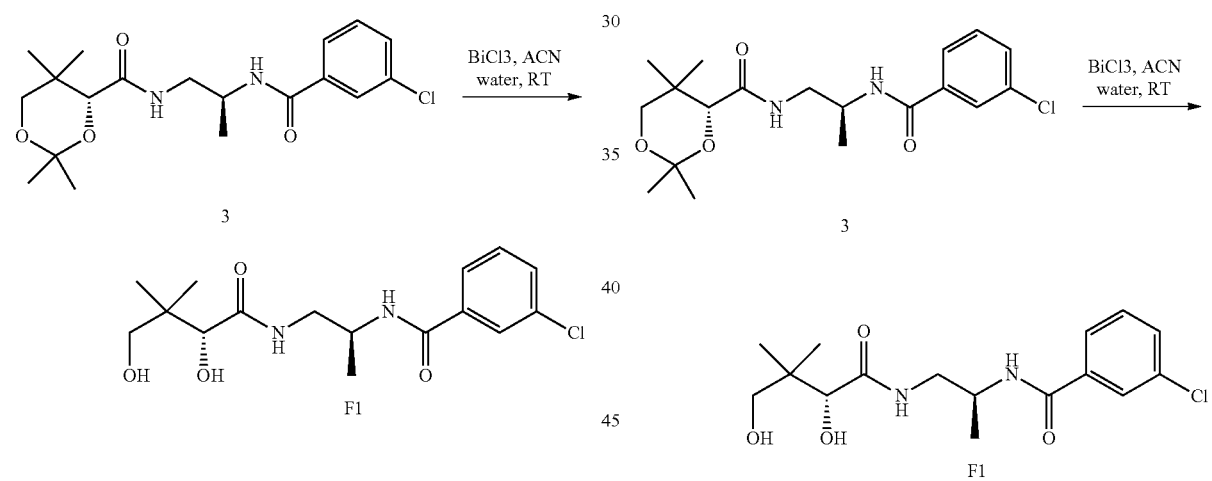

Procedure: Same as general procedure A with (R)-2,2,5,5-Tetramethyl-[1,3]dioxane-4-carboxylic acid ((S)-2-amino-propyl)-amide (1) (100 mg, 0.409 mmol) and 3-Chloro-benzoic acid (2) (76.89 mg, 0.491 mmol) to afford (R)-2,2,5,5-Tetramethyl-[1,3]dioxane-4-carboxylic acid [(S)-2-(3-chloro-benzoylamino)-propyl]-amide (3) as gum in 95.72% yield, 150 mg.

Synthesis of (2R)—N-[(2S)-2-[(3-chlorophenyl)formamido]propyl]-2,4-dihydroxy-3,3-dimethylbutanamide (F1)

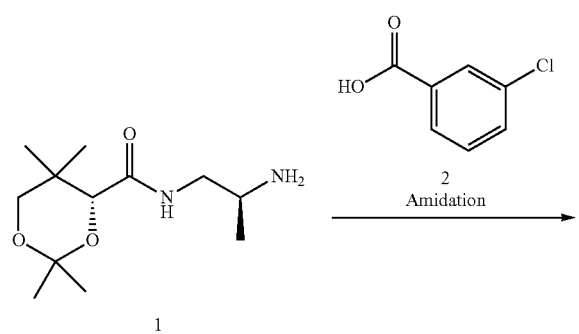

Procedure: Same as general procedure B with (R)-2,2,5,5-Tetramethyl-[1,3]dioxane-4-carboxylic acid [(S)-2-(3-chloro-benzoylamino)-propyl]-amide (3) (150 mg, 0.392 mmol) to afford (2R)—N-[(2S)-2-[(3-chlorophenyl)formamido]propyl]-2,4-dihydroxy-3,3-dimethylbutanamide (F1) as off white solid in 70.74% yield, 95 mg. $^1$H NMR (400 MHz, DMSO-d$_6$) δ 8.35 (d, J=7.72 Hz, 1H), 7.85-7.81 (m, 2H), 7.77 (d, J=7.76 Hz, 1H), 7.58 (d, J=8 Hz, 1H), 7.49 (t, J=7.84 Hz, 1H), 5.40 (d, J=5.44 Hz, 1H), 4.43 (t, J=5.6 Hz, 1H), 4.11-4.06 (m, 1H), 3.73 (d, J=5.44 Hz, 1H), 3.33-3.24 (m, 2H), 3.21-3.11 (m, 2H), 1.11 (d, J=6.64 Hz, 3H), 0.75 (s, 3H), 0.73 (s, 3H). LCMS (HCOOH:ACN): M+H=343, R$_t$=1.41 min in 3 mins run.

Example 7: Synthesis of (2R)—N-[(2S)-2-[(3-chloro-4-fluorophenyl)formamido]propyl]-2,4-dihydroxy-3,3-dimethylbutanamide (G1)

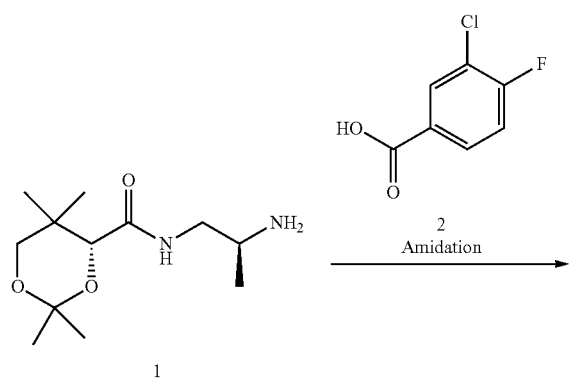

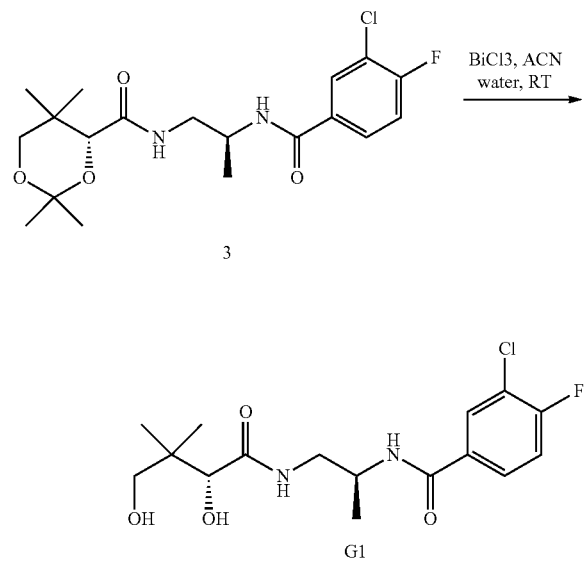

Synthesis of (R)-2,2,5,5-Tetramethyl-[1,3]dioxane-4-carboxylic acid [(S)-2-(3-chloro-4-fluoro-benzoylamino)-propyl]-amide (3)

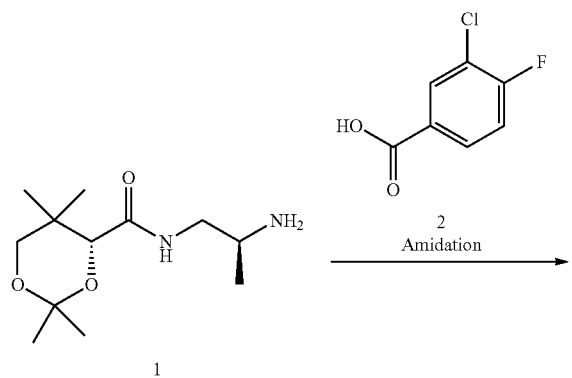

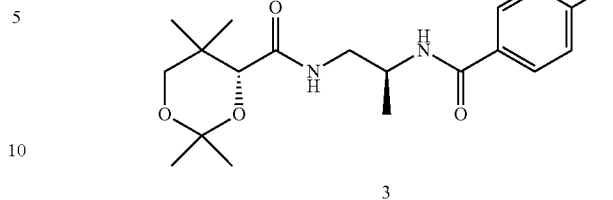

Procedure: Same as general procedure A with (R)-2,2,5,5-Tetramethyl-[1,3]dioxane-4-carboxylic acid ((S)-2-amino-propyl)-amide (1) (100 mg, 0.409 mmol) and 3-Chloro-4-fluoro-benzoic acid (2) (71.415 mg, 0.491 mmol) to afford (R)-2,2,5,5-Tetramethyl-[1,3]dioxane-4-carboxylic acid [(S)-2-(3-chloro-4-fluoro-benzoylamino)-propyl]-amide (3) as gum in 91.46% yield, 150 mg.

Synthesis of (2R)—N-[(2S)-2-[(3-chloro-4-fluorophenyl)formamido]propyl]-2,4-dihydroxy-3,3-dimethylbutanamide (G1)

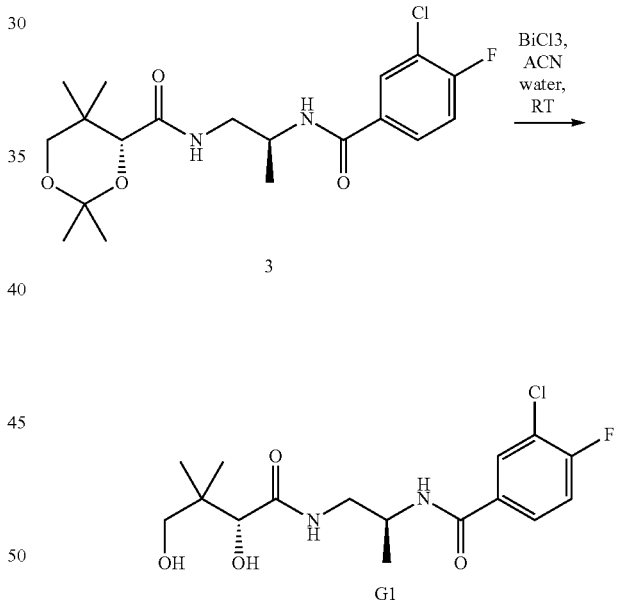

Procedure: Same as general procedure B with (R)-2,2,5,5-Tetramethyl-[1,3]dioxane-4-carboxylic acid [(S)-2-(3-chloro-4-fluoro-benzoylamino)-propyl]-amide (3) (150 mg, 0.374 mmol) to afford (2R)—N-[(2S)-2-[(3-chloro-4-fluorophenyl)formamido]propyl]-2,4-dihydroxy-3,3-dimethylbutanamide (G1) as white solid in 37.04% yield, 50 mg. $^1$H NMR (400 MHz, DMSO-$d_6$) δ 8.35 (d, J=7.64 Hz, 1H), 8.03 (d, J=5.68 Hz, 1H), 7.86-7.80 (m, 2H), 7.52 (t, J=8.84 Hz, 1H), 5.39 (d, J=5.24 Hz, 1H), 4.43 (t, J=5.22 Hz, 1H), 4.11-4.06 (m, 1H), 3.73 (d, J=5.24 Hz, 1H), 3.31-3.24 (m, 2H), 3.19-3.11 (m, 2H), 1.11 (d, J=6.64 Hz, 3H), 0.74 (s, 3H), 0.73 (s, 3H). LCMS (HCOOH:ACN): M+H=361, $R_t$=1.43 min in 3 mins run.

Example 9: Synthesis of (2R)—N-[(2S)-2-[(3,4-difluorophenyl)formamido]propyl]-2,4-dihydroxy-3,3-dimethylbutanamide (H1)

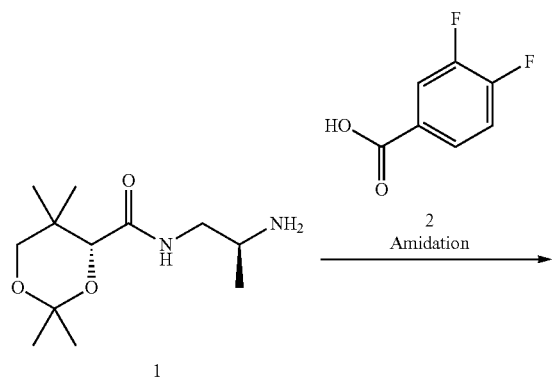

Synthesis of (R)-2,2,5,5-Tetramethyl-[1,3]dioxane-4-carboxylic acid [(S)-2-(3,4-difluoro-benzoylamino) propyl]-amide (3)

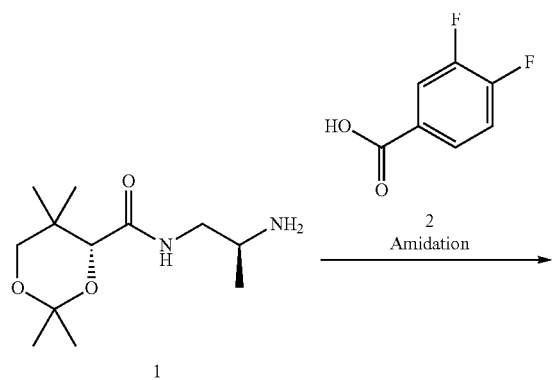

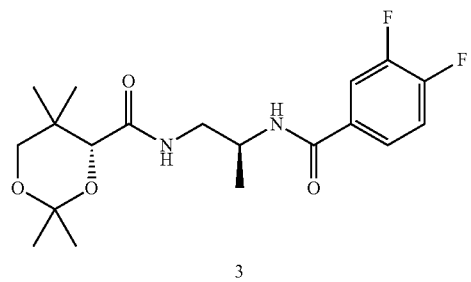

Procedure: Same as general procedure A with (R)-2,2,5,5-Tetramethyl-[1,3]dioxane-4-carboxylic acid ((S)-2-amino-propyl)-amide (1) (75 mg, 0.307 mmol) and 3,4-Difluoro-benzoic acid (2) (48.6 mg, 0.307 mmol) to afford (R)-2,2,5,5-Tetramethyl-[1,3]dioxane-4-carboxylic acid [(S)-2-(3,4-difluoro-benzoylamino)-propyl]-amide (3) as gum in 60.09% yield, 71 mg.

Synthesis of (2R)—N-[(2S)-2-[(3,4-difluorophenyl)formamido]propyl]-2,4-dihydroxy-3,3-dimethyl-butanamide (H1)

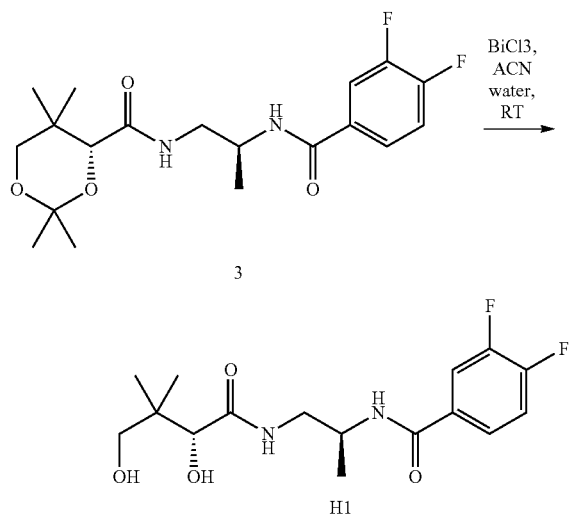

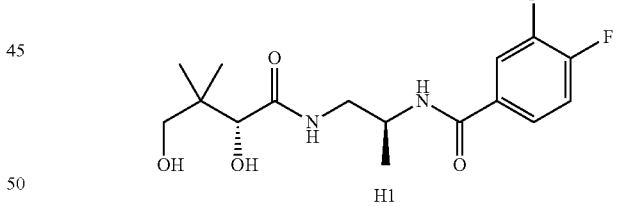

Procedure: Same as general procedure B with (R)-2,2,5,5-Tetramethyl-[1,3]dioxane-4-carboxylic acid [(S)-2-(3,4-difluoro-benzoylamino)-propyl]-amide (3) (71 mg, 0.185 mmol) to afford (2R)—N-[(2S)-2-[(3,4-difluorophenyl)formamido]propyl]-2,4-dihydroxy-3,3-dimethylbutanamide (H1) as off white sticky solid in 66.04% yield, 42 mg. $^1$H NMR (400 MHz, DMSO-$d_6$) δ 8.32 (d, J=7.8 Hz, 1H), 7.90-7.80 (M, 2H), 7.69 (brs, 1H), 7.59-7.52 (m, 1H), 5.41 (d, J=5.36 Hz, 1H), 4.44 (brs, 1H), 4.10-4.06 (m, 1H), 3.72 (d, J=5.36 Hz, 1H), 3.28-3.10 (m, 4H), 1.11 (d, J=6.48 Hz, 3H), 0.73 (S, 6H). LCMS (HCOOH:ACN): M+H=345, $R_t$=1.43 min in 3 mins run.

Example 10: Synthesis of (2R)—N-[(2S)-2-[(5-chloro-2-fluorophenyl)formamido]propyl]-2,4-dihydroxy-3,3-dimethylbutanamide (I1)

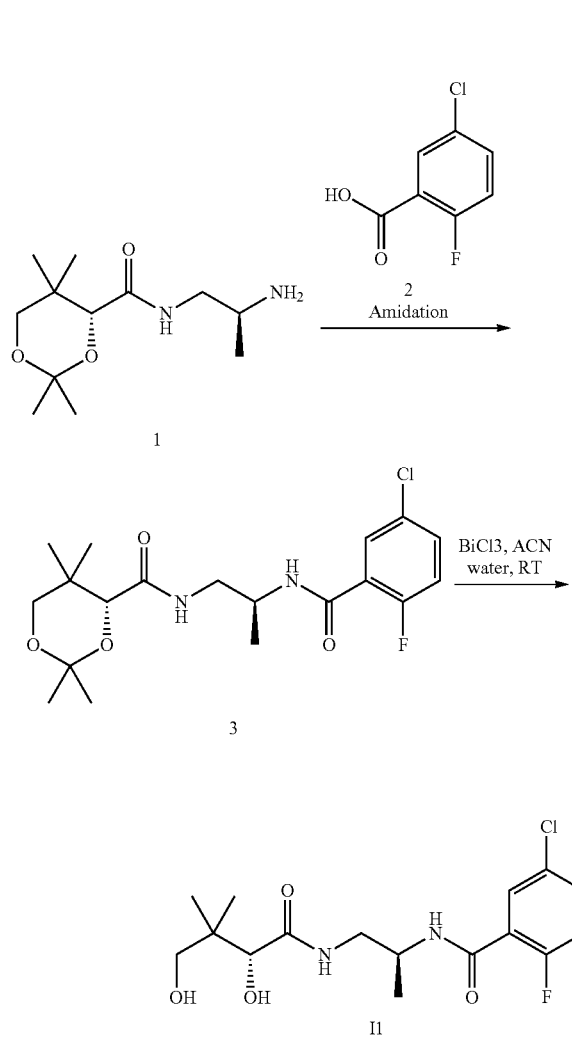

Synthesis of (R)-2,2,5,5-Tetramethyl-[1,3]dioxane-4-carboxylic acid [(S)-2-(5-chloro-2-fluoro-benzoylamino)-propyl]-amide (3)

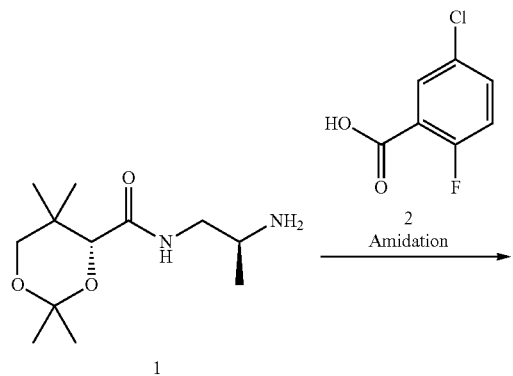

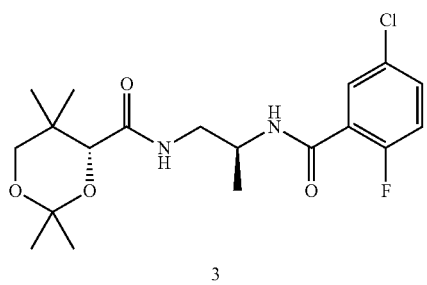

Procedure: Same as general procedure A with (R)-2,2,5,5-Tetramethyl-[1,3]dioxane-4-carboxylic acid ((S)-2-amino-propyl)-amide (1) (75 mg, 0.307 mmol) and 5-Chloro-2-fluoro-benzoic acid (2) (53.58 mg, 0.307 mmol) to afford (R)-2,2,5,5-Tetramethyl-[1,3]dioxane-4-carboxylic acid [(S)-2-(5-chloro-2-fluoro-benzoylamino)-propyl]-amide (3) as gum in 69.08% yield, 85 mg.

Synthesis of (2R)—N-[(2S)-2-[(5-chloro-2-fluorophenyl)formamido]propyl]-2,4-dihydroxy-3,3-dimethylbutanamide (I1)

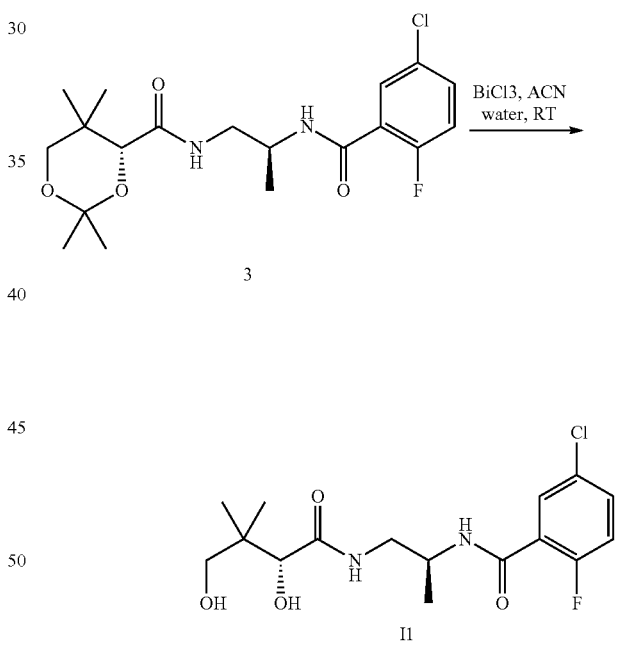

Procedure: Same as general procedure B with (R)-2,2,5,5-Tetramethyl-[1,3]dioxane-4-carboxylic acid [(S)-2-(5-chloro-2-fluoro-benzoylamino)-propyl]-amide (3) (80 mg, 0.2 mmol) to afford (2R)—N-[(2S)-2-[(5-chloro-2-fluoro-phenyl)formamido]propyl]-2,4-dihydroxy-3,3-dimethyl-butanamide (I1) as colorless sticky gum in 53.13% yield, 40 mg. $^1$H NMR (400 MHz, DMSO-$d_6$) δ 8.29 (d, J=6.88 Hz, 1H), 7.83 (brs, 1H), 7.60-7.58 (m, 2H), 7.35 (t, J=9.18 Hz, 1H), 5.42 (d, J=5 Hz, 1H), 4.45 (brs, 1H), 4.06-4.02 (m, 1H), 3.73 (d, J=5 Hz, 1H), 3.30-3.25 (m, 2H), 3.17-3.12 (m, 2H), 1.10 (d, J=6.4 Hz, 3H), 0.77 (s, 3H), 0.76 (s, 3H). LCMS (HCOOH:ACN): M+H=361, $R_t$=1.43 min in 3 mins run.

Example 11: Synthesis of (2R)—N-[(2S)-2-[(2,5-difluorophenyl)formamido]propyl]-2,4-dihydroxy-3,3-dimethylbutanamide (J1)

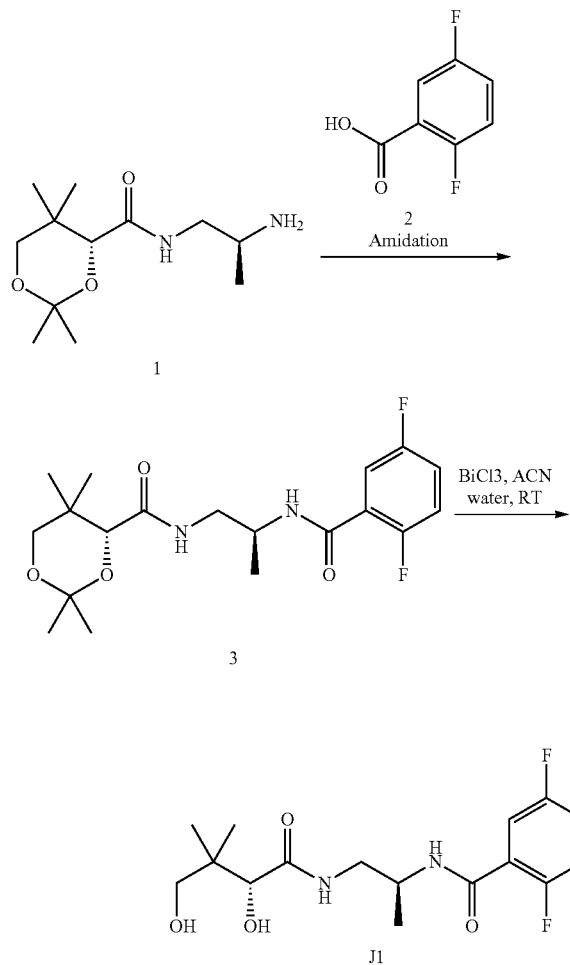

Synthesis of (R)-2,2,5,5-Tetramethyl-[1,3]dioxane-4-carboxylic acid [(S)-2-(2,5-difluoro-benzoylamino)-propyl]-amide (3)

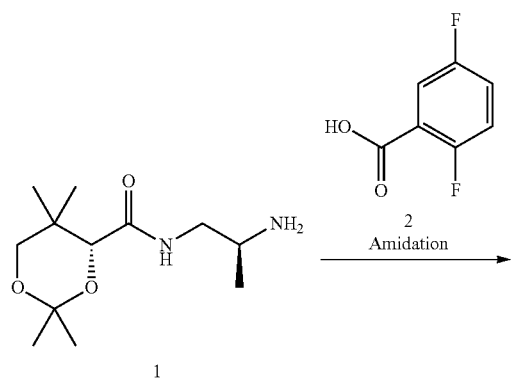

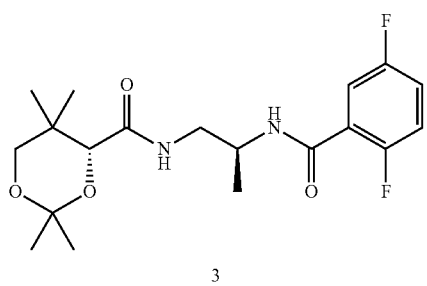

Procedure: Same as general procedure A with (R)-2,2,5,5-Tetramethyl-[1,3]dioxane-4-carboxylic acid ((S)-2-amino-propyl)-amide (1) (75 mg, 0.307 mmol) and 2,5-Difluoro-benzoic acid (2) (48.53 mg, 0.307 mmol) to afford (R)-2,2,5,5-Tetramethyl-[1,3]dioxane-4-carboxylic acid [(S)-2-(2,5-difluoro-benzoylamino)-propyl]-amide (3) as gum in 67.8% yield, 80 mg.

Synthesis of (2R)—N-[(2S)-2-[(2,5-difluorophenyl)formamido]propyl]-2,4-dihydroxy-3,3-dimethylbutanamide (J1)

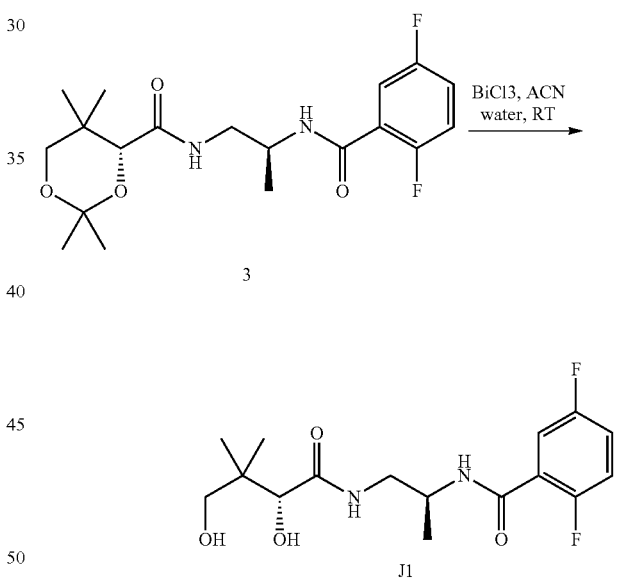

Procedure: Same as general procedure B with (R)-2,2,5,5-Tetramethyl-[1,3]dioxane-4-carboxylic acid [(S)-2-(2,5-difluoro-benzoylamino)-propyl]-amide (3) (70 mg, 0.182 mmol) to afford (2R)—N-[(2S)-2-[(2,5-difluorophenyl)formamido]propyl]-2,4-dihydroxy-3,3-dimethylbutanamide (J1) as colorless sticky gum in 61.34% yield, 45 mg. $^1$H NMR (400 MHz, DMSO-$d_6$) δ 8.25 (d, J=7.16 Hz, 1H), 7.84 (t, J=5.92 Hz, 1H), 7.41-7.34 (m, 3H), 5.41 (d, J=5.48 Hz, 1H), 4.45 (t, J=5.6 Hz, 1H), 4.07-4.02 (m, 1H), 3.73 (d, J=5.48 Hz, 1H), 3.32-3.24 (m, 2H), 3.19-3.12 (m, 2H), 1.10 (d, J=6.6 Hz, 3H), 0.77 (s, 3H), 0.76 (s, 3H). LCMS (HCOOH:ACN): M+H=345, $R_t$=1.37 min in 3 mins run.

Example 12: Synthesis of (2S)-2,4-dihydroxy-3,3-dimethyl-N-[(2R)-2-[(2,4,5-trifluorophenyl)-formamido]propyl]butanamide (A2)
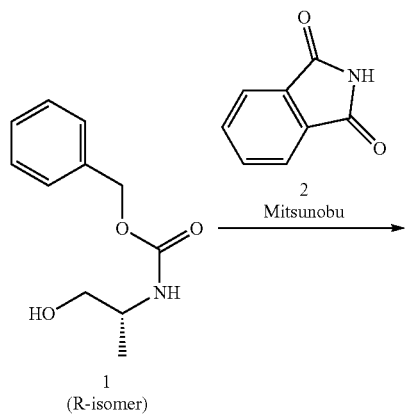
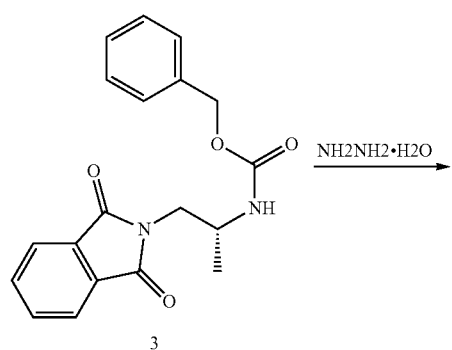
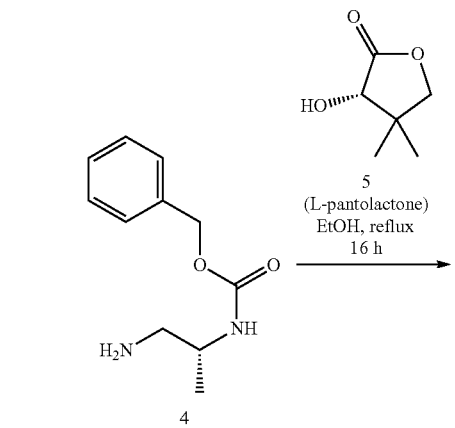
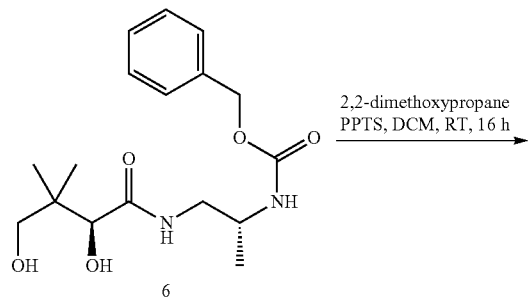
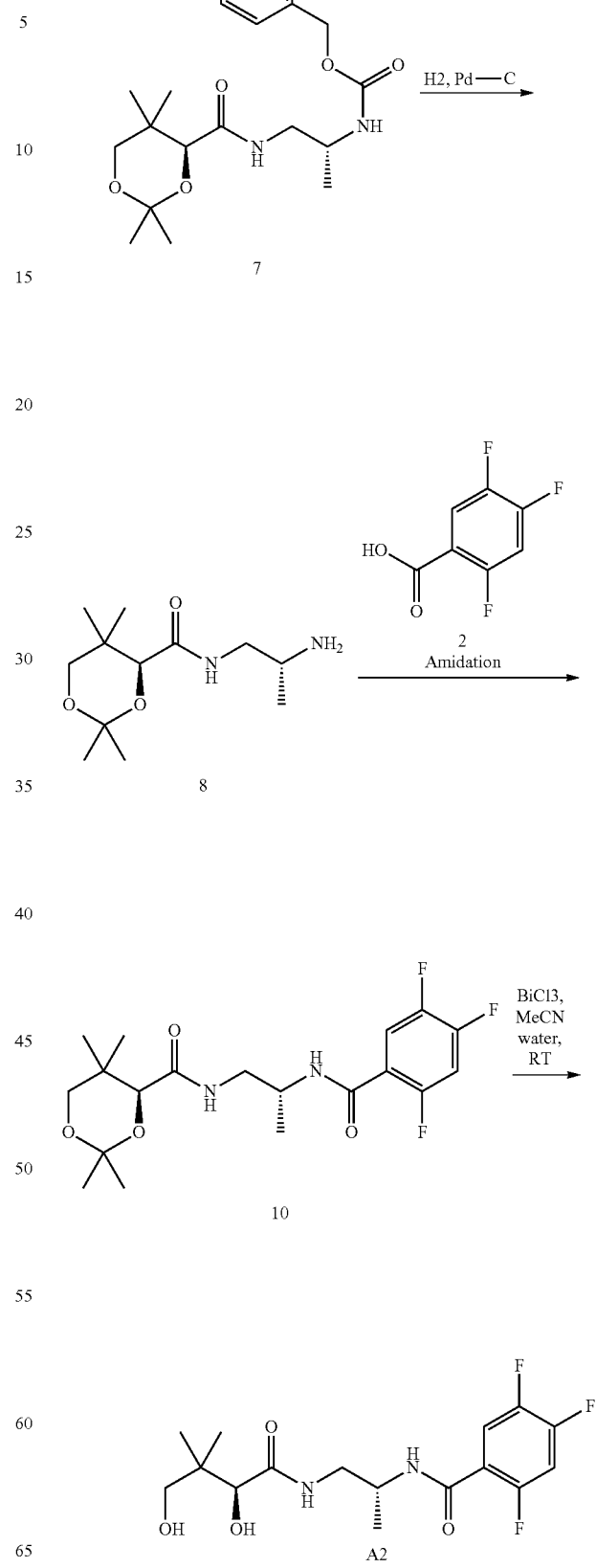

Synthesis of [(R)-2-(1,3-Dioxo-1,3-dihydro-isoindol-2-yl)-1-methyl-ethyl]-carbamic acid benzyl ester (3)

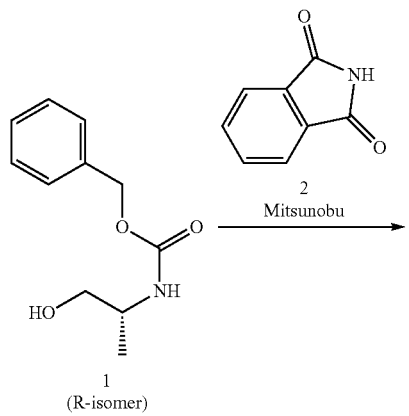

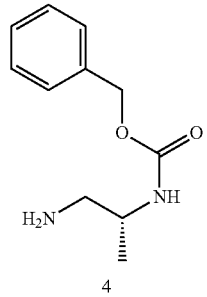

Procedure: Same as ((S)-2-Amino-1-methyl-ethyl)-carbamic acid benzyl ester (step 2 of A1 synthesis) with [(R)-2-(1,3-Dioxo-1,3-dihydro-isoindol-2-yl)-1-methyl-ethyl]-carbamic acid benzyl ester (3) (2.5 g, 7.388 mmol) to afford ((R)-2-Amino-1-methyl-ethyl)-carbamic acid benzyl ester (4) as colorless gum in 97.49% yield, 1.5 g.

Synthesis of [(R)-2-((S)-2,4-Dihydroxy-3,3-dimethyl-butyrylamino)-1-methyl-ethyl]-carbamic acid benzyl ester (6**)

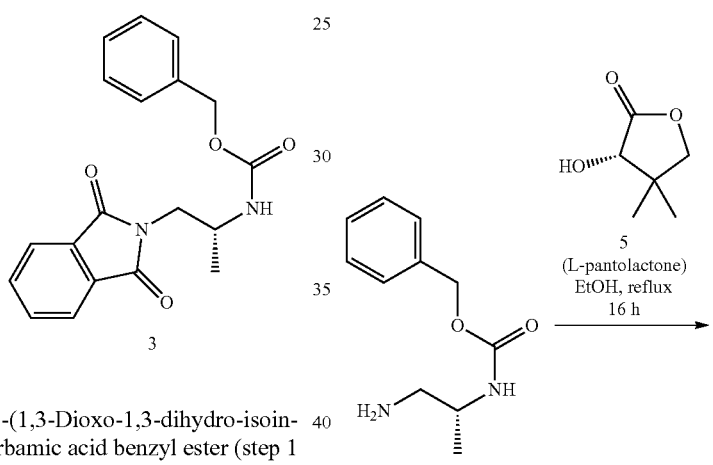

Procedure: Same as [(S)-2-(1,3-Dioxo-1,3-dihydro-isoindol-2-yl)-1-methyl-ethyl]-carbamic acid benzyl ester (step 1 of A1 synthesis) with ((R)-2-Hydroxy-1-methyl-ethyl)-carbamic acid benzyl ester (1) (1.5 g, 7.168 mmol) to afford [(R)-2-(1,3-Dioxo-1,3-dihydro-isoindol-2-yl)-1-methyl-ethyl]-carbamic acid benzyl ester (3) as off white solid in 82.46% yield, 2 g.

Synthesis of ((R)-2-Amino-1-methyl-ethyl)-carbamic acid benzyl ester (4)

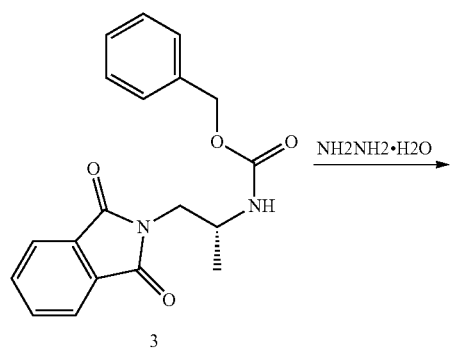

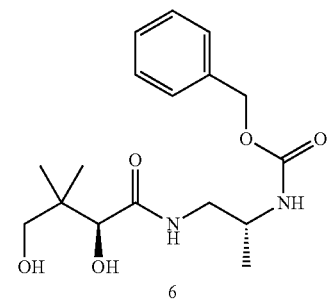

Procedure: Same as [(S)-2-((R)-2,4-Dihydroxy-3,3-dimethyl-butyrylamino)-1-methyl-ethyl]-carbamic acid benzyl ester (step 3 of A1 synthesis) with ((R)-2-Amino-1-methyl-ethyl)-carbamic acid benzyl ester (4) (300 mg, 1.441 mmol) and L-(+)-Pantolactone* (5) (375 mg, 2.881 mmol) to afford [(R)-2-((S)-2,4-Dihydroxy-3,3-dimethyl-butyrylamino)-1-methyl-ethyl]-carbamic acid benzyl ester (6**) as colorless gum in 57.44% yield, 280 mg.

* L-(+)-Pantolactone we received was not enantiomerically pure.

** The product 6 was obtained as a mixture (~1:1) of [(R)-2-((S)-2,4-Dihydroxy-3,3-dimethyl-butyrylamino)-1- methyl-ethyl]-carbamic acid benzyl ester and [(R)-2-((R)-2,4-Dihydroxy-3,3-dimethyl-butyrylamino)-1-methyl-ethyl]-carbamic acid benzyl ester. The mixture was used and diastereomer separation performed on the final product.

Synthesis of {(R)-1-Methyl-2-[((S)-2,2,5,5-tetramethyl-[1,3]dioxane-4-carbonyl)-amino]-ethyl}-carbamic acid benzyl ester (7**)

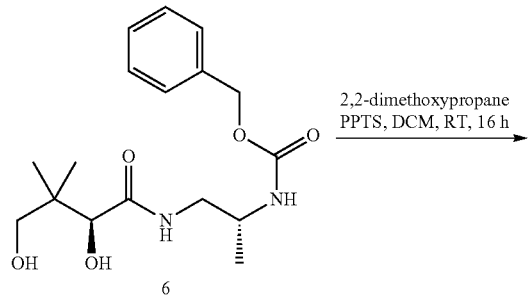

Procedure: Same as {(S)-1-Methyl-2-[((R)-2,2,5,5-tetramethyl-[1,3]dioxane-4-carbonyl)-amino]-ethyl}-carbamic acid benzyl ester (step 4 of A1 synthesis) with [(R)-2-((S)-2,4-Dihydroxy-3,3-dimethyl-butyrylamino)-1-methyl-ethyl]-carbamic acid benzyl ester (6) (330 mg, 2.881 mmol) to afford {(R)-1-Methyl-2-[((S)-2,2,5,5-tetramethyl-[1,3]dioxane-4-carbonyl)-amino]-ethyl}-carbamic acid benzyl ester (7) as colorless gum in 75.86% yield, 280 mg.  Mixture of two diastereomers Synthesis of (S)-2,2,5,5-Tetramethyl-[1,3]dioxane-4-carboxylic acid ((R)-2-amino-propyl)-amide (8))

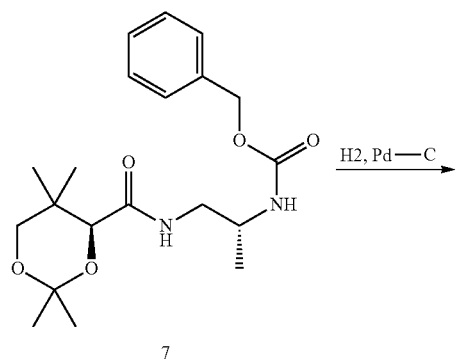

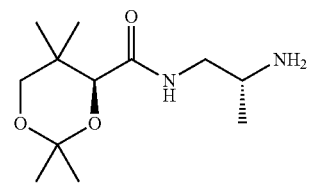

Procedure: Same as (R)-2,2,5,5-Tetramethyl-[1,3]dioxane-4-carboxylic acid ((S)-2-amino-propyl)-amide (step 5 of A1 synthesis) with {(R)-1-Methyl-2-[((S)-2,2,5,5-tetramethyl-[1,3]dioxane-4-carbonyl)-amino]-ethyl}-carbamic acid benzyl ester (7) (280 mg, 0.74 mmol) to afford (S)-2,2,5,5-Tetramethyl-[1,3]dioxane-4-carboxylic acid ((R)-2-amino-propyl)-amide (8) as colorless gum in 99.56% yield, 180 mg.  Mixture of two diastereomers Synthesis of (S)-2,2,5,5-Tetramethyl-[1,3]dioxane-4-carboxylic acid [(R)-2-(2,4,5-trifluoro-benzoylamino)-propyl]-amide (10)

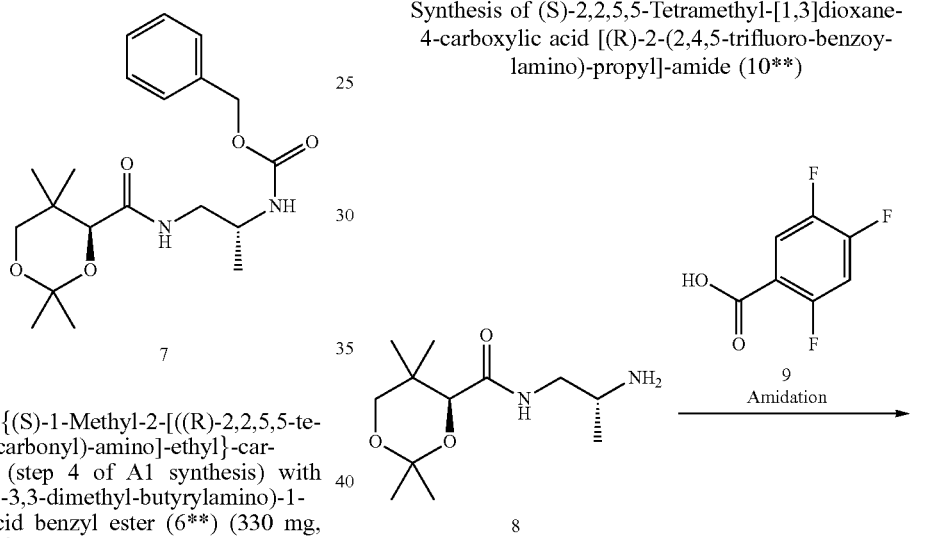

Procedure: Same as general procedure A with (S)-2,2,5,5-Tetramethyl-[1,3]dioxane-4-carboxylic acid ((R)-2-amino-propyl)-amide (8) (180 mg, 0.737 mmol) and 2,4,5-Trifluoro-benzoic acid (9) (129.75 mg, 0.737 mmol) to afford (S)-2,2,5,5-Tetramethyl-[1,3]dioxane-4-carboxylic acid [(R)-2-(2,4,5-trifluoro-benzoylamino)-propyl]-amide (10) as colorless gum in 94.44% yield, 280 mg. ** Mixture of two diastereomers Synthesis of (2S)-2,4-dihydroxy-3,3-dimethyl-N-[(2R)-2-[(2,4,5-trifluorophenyl) formamido]-propyl]butanamide (A2):

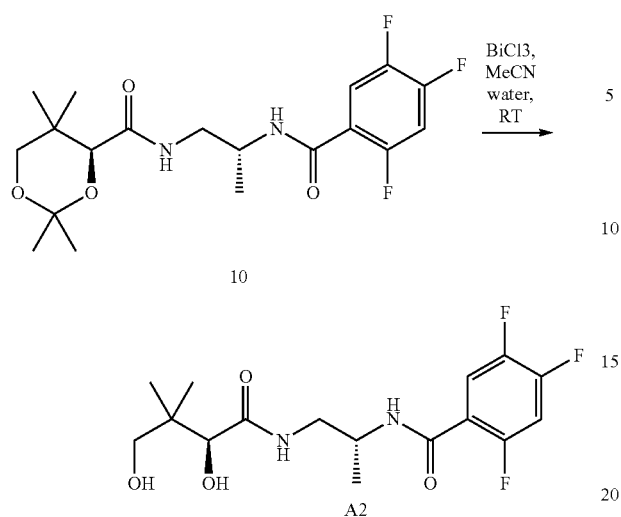

Procedure: Same as general procedure B with (S)-2,2,5,5-Tetramethyl-[1,3]dioxane-4-carboxylic acid [(R)-2-(2,4,5-trifluoro-benzoylamino)-propyl]-amide (10) (280 mg, 0.696 mmol) and final diastereomer separation by prep HPLC (Column Name: Chiralpak IC (4.6×250 mm), 5µ, ARD/K/7788, Mobile Phase: Hexane/EtOH/IPamine: 80/20/0.1, Flow Rate: 1.0 ml/min, Solubility: MeOH) afford (2S)-2,4-dihydroxy-3,3-dimethyl-N-[(2R)-2-[(2,4,5-trifluorophenyl)formamido]propyl]butanamide (A2) (faster moving fraction) as colorless gum in 13.88% yield, 35 mg. $^1$H NMR (400 MHz, DMSO-$d_6$) δ 8.24 (d, J=7.56 Hz, 1H), 7.84 (t, J=5.88 Hz, 1H), 7.72-7.63 (m, 2H), 5.41 (d, J=5.48 Hz, 1H), 4.44 (t, J=5.58 Hz, 1H), 4.07-4.03 (m, 1H), 3.73 (d, J=5.48 Hz, 1H), 3.32-3.24 (m, 2H), 3.19-3.12 (m, 2H), 1.10 (d, J=6.64 Hz, 3H), 0.77 (s, 3H), 0.76 (s, 3H). LCMS (HCOOH:ACN): M+H=363, $R_t$=1.38 min in 3 mins run.  Mixture of two diastereomers Example 13: Synthesis of (2R)-2,4-dihydroxy-3,3-dimethyl-N-[(2R)-2-[(2,4,5-trifluorophenyl)-formamido]propyl]butanamide (A3)

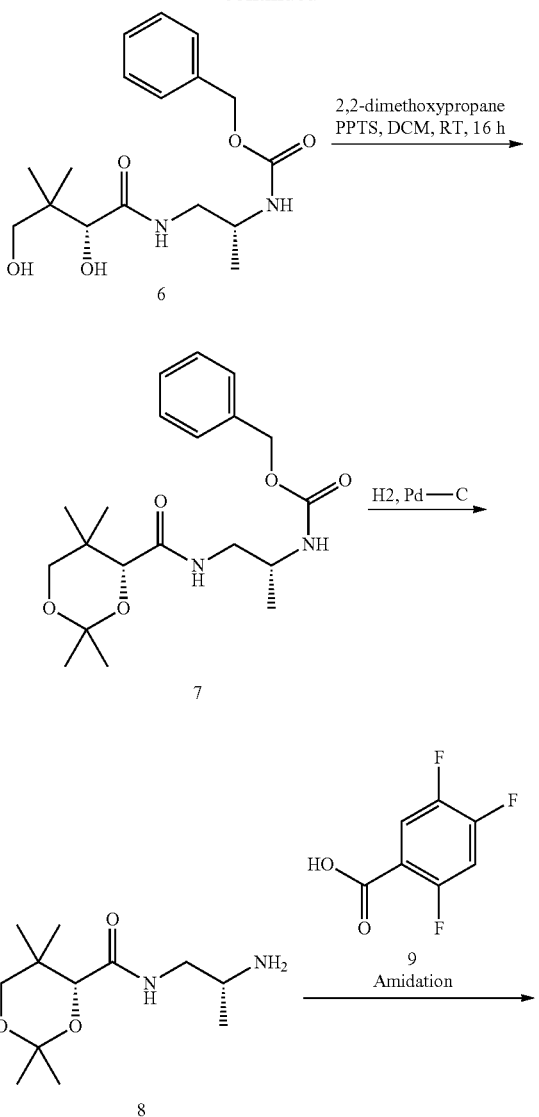

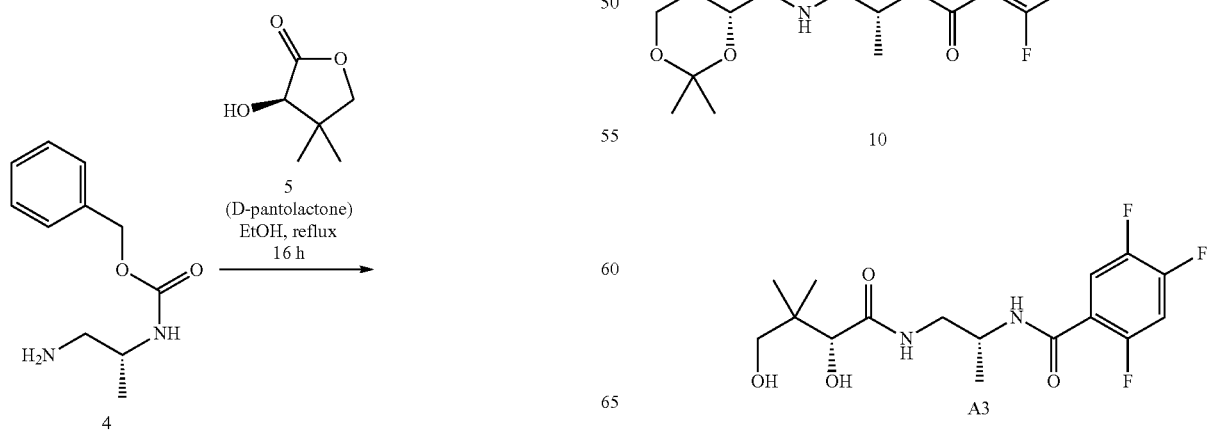

Synthesis of [(R)-2-((R)-2,4-Dihydroxy-3,3-dimethyl-butyrylamino)-1-methyl-ethyl]-carbamic acid benzyl ester (6)

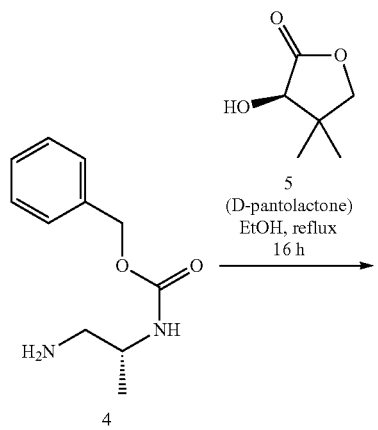

Procedure: Same as [(S)-2-((R)-2,4-Dihydroxy-3,3-dimethyl-butyrylamino)-1-methyl-ethyl]-carbamic acid benzyl ester (step 3 of A1 synthesis) with ((R)-2-Amino-1-methyl-ethyl)-carbamic acid benzyl ester (4) (300 mg, 1.441 mmol) and D-(−)-Pantolactone (5) (375 mg, 2.881 mmol) to afford [(R)-2-((R)-2,4-Dihydroxy-3,3-dimethyl-butyrylamino)-1-methyl-ethyl]-carbamic acid benzyl ester (6) as colorless gum in 47.18% yield, 230 mg.

Synthesis of {(R)-1-Methyl-2-[((R)-2,2,5,5-tetramethyl-[1,3]dioxane-4-carbonyl)-amino]-ethyl}-carbamic acid benzyl ester (7)

Procedure: Same as {(S)-1-Methyl-2-[((R)-2,2,5,5-tetramethyl-[1,3]dioxane-4-carbonyl)-amino]-ethyl}-carbamic acid benzyl ester (step 4 of A1 synthesis) with [(R)-2-((R)-2,4-Dihydroxy-3,3-dimethyl-butyrylamino)-1-methyl-ethyl]-carbamic acid benzyl ester (6) (240 mg, 0.709 mmol) to afford {(R)-1-Methyl-2-[((R)-2,2,5,5-tetramethyl-[1,3]dioxane-4-carbonyl)-amino]-ethyl}-carbamic acid benzyl ester (7) as off white solid in 85.69% yield, 230 mg.

Synthesis of (R)-2,2,5,5-Tetramethyl-[1,3]dioxane-4-carboxylic acid ((R)-2-amino-propyl)-amide (8)

Procedure: Same as (R)-2,2,5,5-Tetramethyl-[1,3]dioxane-4-carboxylic acid ((S)-2-amino-propyl)-amide (step 5 of A1 synthesis) with {(R)-1-Methyl-2-[((R)-2,2,5,5-tetramethyl-[1,3]dioxane-4-carbonyl)-amino]-ethyl}-carbamic acid benzyl ester (7) (230 mg, 0.608 mmol) to afford (R)-2,2,5,5-Tetramethyl-[1,3]dioxane-4-carboxylic acid ((R)-2-amino-propyl)-amide (8) as colorless gum in 94.17% yield, 140 mg.

Synthesis of (R)-2,2,5,5-Tetramethyl-[1,3]dioxane-4-carboxylic acid [(R)-2-(2,4,5-trifluoro-benzoylamino)-propyl]-amide (10)

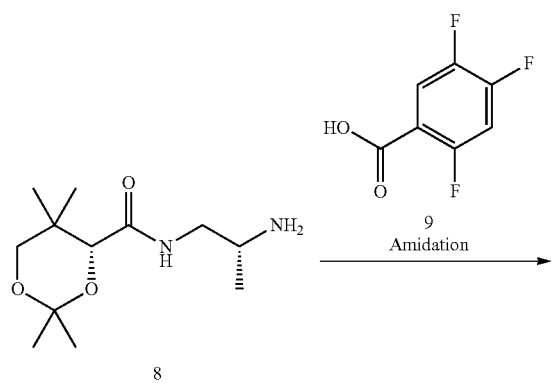

Procedure: Same as general procedure A with (R)-2,2,5,5-Tetramethyl-[1,3]dioxane-4-carboxylic acid ((R)-2-amino-propyl)-amide (8) (140 mg, 0.573 mmol) and 2,4,5-Trifluoro-benzoic acid (9) (100.917 mg, 0.573 mmol) to afford (R)-2,2,5,5-Tetramethyl-[1,3]dioxane-4-carboxylic acid [(R)-2-(2,4,5-trifluoro-benzoylamino)-propyl]-amide (10) as colorless gum in 91.06% yield, 210 mg.

Synthesis of (2R)-2,4-dihydroxy-3,3-dimethyl-N-[(2R)-2-[(2,4,5-trifluorophenyl)formamido]-propyl]butanamide (A3)

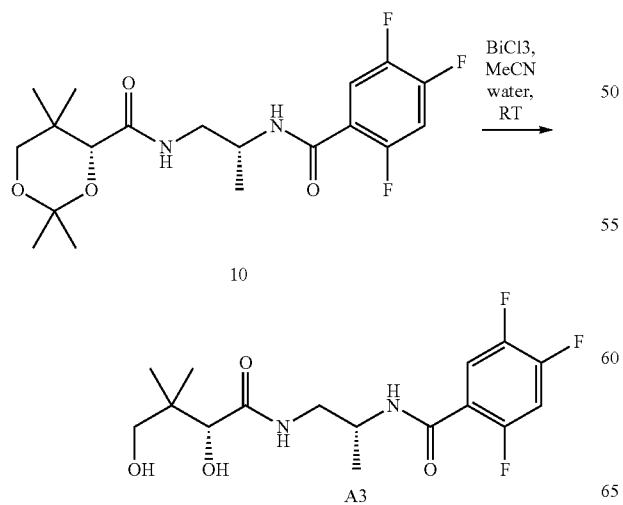

Procedure: Same as general procedure B with (R)-2,2,5,5-Tetramethyl-[1,3]dioxane-4-carboxylic acid [(R)-2-(2,4,5-trifluoro-benzoylamino)-propyl]-amide (10) (210 mg, 0.522 mmol) to afford (2R)-2,4-dihydroxy-3,3-dimethyl-N-[(2R)-2-[(2,4,5-trifluorophenyl)formamido]propyl]-butanamide (A3) as light brown sticky gum in 47.6% yield, 90 mg. $^1$H NMR (400 MHz, DMSO-$d_6$) δ 8.23 (d, J=8 Hz, 1H), 7.83 (t, J=5.88 Hz, 1H), 7.70-7.64 (m, 2H), 5.42 (d, J=5.4 Hz, 1H), 4.45 (t, J=5.5 Hz, 1H), 4.04-4.00 (m, 1H), 3.72 (d, J=5.4 Hz, 1H), 3.31-3.26 (m, 2H), 3.16-3.06 (m, 2H), 1.09 (d, J=6.56 Hz, 3H), 0.79 (s, 3H), 0.75 (s, 3H). LCMS (HCOOH:ACN): M+H=363, $R_t$=1.38 min in 3 mins run.

Example 14: Synthesis of (2S)-2,4-dihydroxy-3,3-dimethyl-N-[(2S)-2-[(2,4,5-trifluorophenyl)-formamido]propyl]butanamide (A4)

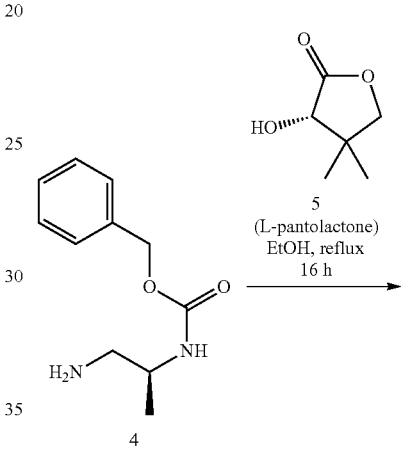

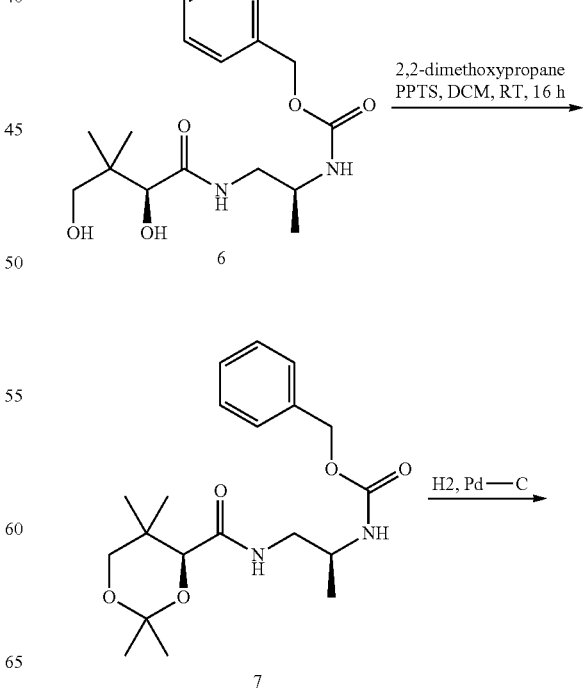

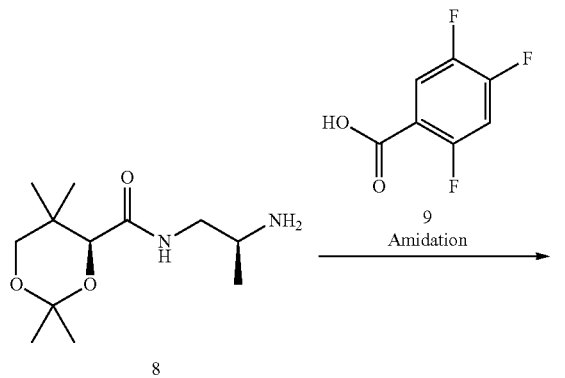

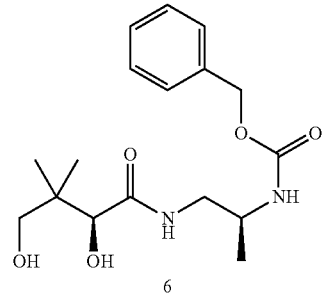

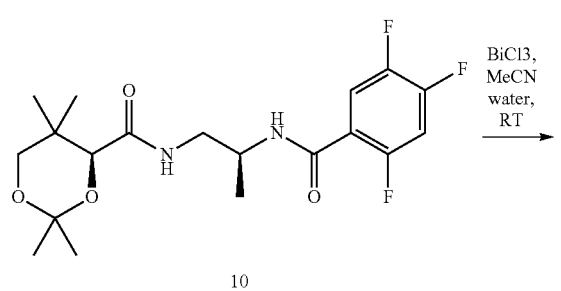

Synthesis of [(S)-2-((S)-2,4-Dihydroxy-3,3-dimethyl-butyrylamino)-1-methyl-ethyl]-carbamic acid benzyl ester (6**)

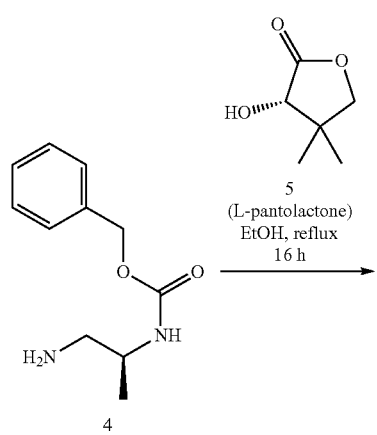

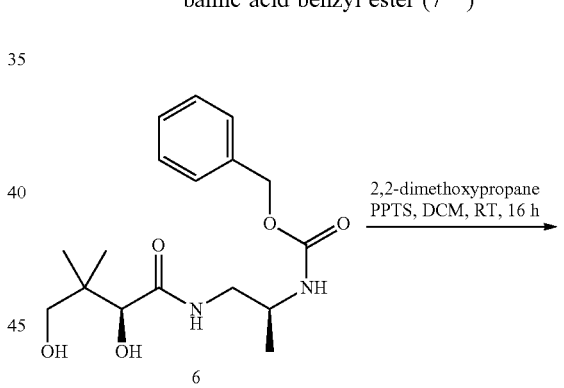

Procedure: Same as [(S)-2-((R)-2,4-Dihydroxy-3,3-dimethyl-butyrylamino)-1-methyl-ethyl]-carbamic acid benzyl ester (step 3 of A1 synthesis) with ((S)-2-Amino-1-methyl-ethyl)-carbamic acid benzyl ester (4) (350 mg, 1.681 mmol) and L-(+)-Pantolactone* (5) (437.42 mg, 3.361 mmol) to afford [(S)-2-((S)-2,4-Dihydroxy-3,3-dimethyl-butyrylamino)-1-methyl-ethyl]-carbamic acid benzyl ester (6**) as colorless gum in 45.72% yield, 260 mg. * L-(+)-Pantolactone turned out not to be enantiomerically pure. ** Product 6 was obtained as a mixture (~1:1) of [(S)-2-((S)-2,4-Dihydroxy-3,3-dimethyl-butyrylamino)-1-methyl-ethyl]-carbamic acid benzyl ester and [(S)-2-((R)-2,4-Dihydroxy-3,3-dimethyl-butyrylamino)-1-methyl-ethyl]-carbamic acid benzyl ester. The mixture was used and diastereomers were separated from the end-product.

Synthesis of {(S)-1-Methyl-2-[((S)-2,2,5,5-tetramethyl-[1,3]dioxane-4-carbonyl)-amino]-ethyl}-carbamic acid benzyl ester (7**)

Procedure: Same as {(S)-1-Methyl-2-[((R)-2,2,5,5-tetramethyl-[1,3]dioxane-4-carbonyl)-amino]-ethyl}-carbamic acid benzyl ester (step 4 of A1 synthesis) with [(S)-2-((S)-2,4-Dihydroxy-3,3-dimethyl-butyrylamino)-1-methyl-ethyl]-carbamic acid benzyl ester (6) (260 mg, 0.768 mmol) to afford {(S)-1-Methyl-2-[((S)-2,2,5,5-tetramethyl-[1,3]dioxane-4-carbonyl)-amino]-ethyl}-carbamic acid benzyl ester (7) as colorless gum in 75.66% yield, 220 mg.  Mixture of two diastereomers Synthesis of (S)-2,2,5,5-Tetramethyl-[1,3]dioxane-4-carboxylic acid ((S)-2-amino-propyl)-amide (8))

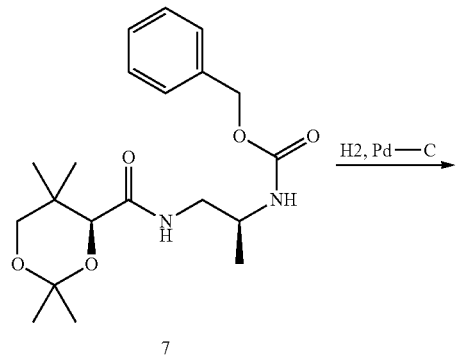

Procedure: Same as (R)-2,2,5,5-Tetramethyl-[1,3]dioxane-4-carboxylic acid ((S)-2-amino-propyl)-amide (step 5 of A1 synthesis) with {(S)-1-Methyl-2-[((S)-2,2,5,5-tetramethyl-[1,3]dioxane-4-carbonyl)-amino]-ethyl}-carbamic acid benzyl ester (7) (220 mg, 0.582 mmol) to afford (S)-2,2,5,5-Tetramethyl-[1,3]dioxane-4-carboxylic acid ((S)-2-amino-propyl)-amide (8) as colorless gum in 91.42% yield, 130 mg.  Mixture of two diastereomers Synthesis of (S)-2,2,5,5-Tetramethyl-[1,3]dioxane-4-carboxylic acid [(S)-2-(2,4,5-trifluoro-benzoylamino)-propyl]-amide (10)

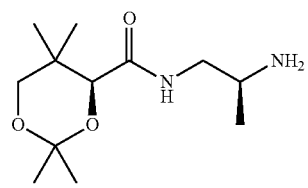

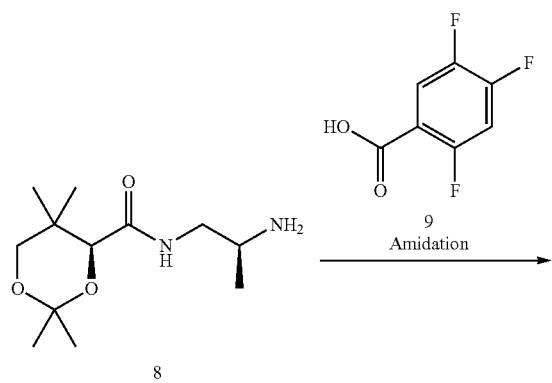

Procedure: Same as general procedure A with (S)-2,2,5,5-Tetramethyl-[1,3]dioxane-4-carboxylic acid ((S)-2-amino-propyl)-amide (8) (130 mg, 0.533 mmol) and 2,4,5-Trifluoro-benzoic acid (9) (93.77 mg, 0.533 mmol) to afford (S)-2,2,5,5-Tetramethyl-[1,3]dioxane-4-carboxylic acid [(S)-2-(2,4,5-trifluoro-benzoylamino)-propyl]-amide (10) as colorless gum in 88.62% yield, 190 mg. ** Mixture of two diastereomers Synthesis of (2S)-2,4-dihydroxy-3,3-dimethyl-N-[(2S)-2-[(2,4,5-trifluorophenyl)formamido]-propyl]butanamide (A4))

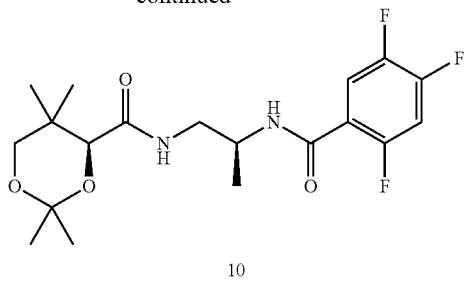

Procedure: Same as general procedure B with (S)-2,2,5,5-Tetramethyl-[1,3]dioxane-4-carboxylic acid [(S)-2-(2,4,5-trifluoro-benzoylamino)-propyl]-amide (10**) (190 mg, 0.472 mmol) and final diastereomer separation by prep HPLC (Column Name: Chiralpak IC (4.6×250 mm), 5µ, ARD/K/7788, Mobile Phase: Hexane/EtOH/IPamine: 80/20/0.1, Flow Rate: 1.0 ml/min, Solubility: MeOH) afford (2S)-2,4-dihydroxy-3,3-dimethyl-N-[(2S)-2-[(2,4,5-trifluorophenyl)formamido]-propyl]butanamide (A4) (faster moving fraction) as colorless gum in 14.61% yield, 25 mg. $^1$H NMR (400 MHz, DMSO-$d_6$) δ 8.23 (d, J=8 Hz, 1H), 7.83 (t, J=5.88 Hz, 1H), 7.70-7.64 (m, 2H), 5.42 (d, J=5.4 Hz, 1H), 4.45 (t, J=5.5 Hz, 1H), 4.04-4.00 (m, 1H), 3.72 (d, J=5.4 Hz, 1H), 3.31-3.26 (m, 2H), 3.16-3.06 (m, 2H), 1.09 (d, J=6.56 Hz, 3H), 0.79 (s, 3H), 0.75 (s, 3H). LCMS (HCOOH:ACN): M+H=363, $R_t$=1.38 min in 3 mins run.

Example 15: Antimalarial Activity

*Plasmodium falciparum* strain NF54 was cultured in Roswell Park Memorial Institute (RPMI) 1640 medium supplemented with 25 mM NaHCO$_3$, 10% human type A serum and 5% (v/v) human type 0 red blood cells (Sanquin, the Netherlands). Replication assays for asexual blood-stage parasites were performed by diluting parasites in RPMI1640 medium with 10% human serum to a parasitemia of 0.83% and a hematocrit of 3%. 30 µl of diluted parasites were combined with 30 µl of compound serially diluted in DMSO and RPMI1640 medium to reach a final DMSO concentration of 0.1% in a total assay volume of 60 µL. Following a 72 h incubation at 37° C., 3% O$_2$, 4% CO$_2$, 30 µL of diluted SYBR® Green reagent was added according to the instructions of the manufacturer (Life Technologies) and fluorescence intensity was quantified using a Biotek Synergy® 2 plate reader. Gametocyte viability assays were initiated by inoculating a culture flask with 1% asexual blood-stage parasites in 5% haematocrit in RPMI1640 medium with 10% human serum. From day 4 to day 9 after inoculation, cultures were treated with 50 mM N-acetylglucosamine to eliminate asexual blood-stage parasites. At day 11 post inoculation, gametocytes (predominantly stage IV) were isolated by Percoll® density gradient centrifugation. Gametocytes were seeded at a density of 5,000 cells/well in a 384 well plate and combined with compound diluted in DMSO and subsequently in RPMI1640 medium to reach a final DMSO concentration of 0.1% in a volume of 60 µL RPMI1640 medium with 10% human serum. Following a 72 h incubation at 37° C., 3% O$_2$, 4% CO$_2$, 30 µL of ONE-Glo® reagent (Promega) was added and luminescence was quantified using a Biotek Synergy 2 reader. IC$_{50}$ values were derived by fitting a four parameter logistic regression model to the data using least squares to find the best fit. Resulting IC$_{50}$ values against *P. falciparum* NF54 asexual blood stage parasites and gametocytes are presented in table 2.

Table 2

Activities of pantothenamide analogues against *P. falciparum* asexual blood stage parasites and gametocytes. The table shows average IC50 values derived from at least two replicate experiments.

| Compound | antimalarial IC$_{50}$ (nM) | |
|---|---|---|
| | asexual blood stages | gametocytes |
| A1 | 2.4 | 8.0 |
| B1 | 6.2 | 21.4 |
| C1 | 7.4 | 2.2 |
| D1 | 2.3 | 0.4 |
| E1 | 1.9 | 2.0 |
| F1 | 2.1 | 0.4 |
| G1 | 3.4 | 0.2 |

Example 16: Metabolic Stability in Human Primary Hepatocytes

Metabolic stability of compounds of the invention was assessed in a hepatocyte relay assay. Human primary hepatocytes (Xenotech) were cultured in collagen coated 96-well plates in Williams E (Gibco® 32551087) supplemented with 1% PenStrep (Gibco 15140-122), 1% Fungizone® (Gibco 15290026), 10% heat-inactivated fetal bovine serum (hiFBS) (Gibco 10270-106), 0.1 IU/ml insulin (Sigma I2643) and 7 µM hydrocortisone hemisuccinate (Sigma H2270) at 37° C. and 5% CO$_2$. Test compounds were added to a final concentration of 10 µM in 0.1 DMSO. Every 24 hours, the cell supernatant was transferred to freshly plated, metabolically full active cells. At regular time intervals, aliquots of supernatants were frozen for future analysis. At the end of the incubation, all samples were thawed and compound levels in time were determined by LC-MS analyses. Data were analysed by linear regression. Resulting clearance values and half-lifes are presented in table 3. The data show that all compounds tested show low clearance in human hepatocytes.

Table 3—Metabolic stability of pantothenamide analogues in human primary cells as assessed in a relay assay. The table shows intrinsic clearance (Clint) expressed as µl/min/10$^6$ cells and half-life expressed in minutes. Values indicate average values from two replicate experiments and their cognate standard deviations (s.d.).

| Compound | Clint (µl/min/10$^6$ cells) | | T½ (mins) | |
|---|---|---|---|---|
| | average | s.d. | average | s.d. |
| A1 | 0.4 | 0.079486 | 3564.5 | 713.9024 |
| B1 | 0.2 | 0.009849 | 6395.3 | 290.2712 |
| C1 | 0.3 | 0.006448 | 5043.1 | 118.2598 |
| E1 | 0.5 | 0.037744 | 2530.1 | 173.8748 |

Example 17: In Vivo Antimalarial Activity

Reduction of existing parasitemia in vivo was investigated using a humanized mouse model for *P. falciparum* infection. Female NODscidIL2Rγnull mice were engrafted by daily intravenous injection of 0.6 ml of human blood for 11 days. Subsequently, mice were infected with *P. falciparum* strain Pf3D70087/N9 by injecting 2.10$^7$ parasites in a volume of 0.2 ml. Four days post infection, mice were treated with a single 50 mg/kg dose of test compound. To this end, compounds were formulated in 70% Tween®-80 (d=1.08 g/ml) and 30% ethanol (d=0.81 g/ml), followed by a 10-fold dilution in H$_2$O and administered by oral gavage. Parasitemia was followed by daily collection of 2 µl tail blood. The hematocrit was determined by fluorescence-activated cell sorting (FACS) and parasitemia by microscopy on >10,000 red blood cells. FIG. 1 shows the in vivo efficacy of pantothenamide analogues. The FIGURE shows parasitemia (% of infected human red blood cells) in time in a humanized mouse model for *P. falciparum* asexual blood stage infection. The compounds indicated at the legend were dosed as a single oral dose of 50 mg/kg at day 4 post infection (indicated by the arrow) and parasitemia was followed for another three days. The data shown in FIG. 1 indicate that all pantothenamide analogues tested show a dramatic reduction in blood stage parasitemia at a single oral dose of 50 mg/kg.

Table 4—In vivo efficacy of pantothenamide analogues determined in female NODscidIL2Rγnull mice infected with *P. falciparum* strain Pf3D70087/N9. The table shows the log reduction in parasitemia.

| Compound | In vivo efficacy log reduction in parasitemia in Pf SCID mouse at 50 mg/kg p.o. 1 × QD |
|---|---|
| A1 | >3 |
| B1 | 2.4 |
| C1 | >3 |
| E1 | >3 |

Comparative Example

A compound denominated MMV689258 was disclosed in WO2016/072854. For this compound metabolic stability and in vivo efficacy data have been generated following the same protocols as described in present examples 16 and 17 respectively. The results are summarized in table 5 below. As can be inferred from this data, the compound denominated MMV689258 has a metabolic stability substantially lower than the compounds of the invention and is substantially less efficacious in vivo.

Table 5—Metabolic stability and in vivo efficacy of MMV689258. Metabolic stability was determined in human primary cells assessed in a relay assay. The table shows intrinsic clearance (Clint) expressed as $\mu l/min/10^6$ cells and half-life expressed in minutes. In vivo efficacy was determined in female NODscidIL2Rγnull mice infected with *P. falciparum* strain Pf3D70087/N9. The table shows the log reduction in parasitemia.

| Compound | Metabolic stability in human hepatocytes | | In vivo efficacy log reduction in parasitemia in Pf SCID mouse at 50 mg/kg p.o. 1 × QD |
|---|---|---|---|
| | Clint (μl/min/ $10^6$ cells) | T½ (mins) | |
| MMV689258 | 0.8 | 1764.2 | 1.5 |

The invention claimed is:

1. A compound selected from the group consisting of the pantothenamide analogues represented by formula (I):

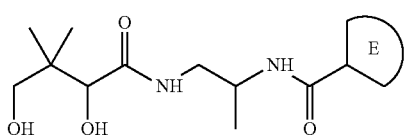

(I)

wherein ring E represents an optionally substituted phenyl ring or a pharmaceutically acceptable salt thereof.

2. The compound according to claim 1, wherein ring E represents phenyl, which may be substituted with 1-3 substituents independently selected from nitril and halo.

3. The compound according to claim 1, wherein ring E represents phenyl substituted with 1-3 substituents independently selected from chloro and fluoro.

4. The compound according to claim 1, wherein ring E represents phenyl substituted with three fluoro.

5. The compound according to claim 1, wherein ring E represents phenyl substituted with 1 nitril group.

6. The compound according to claim 1, which is selected from the compounds (A)-(J) and (A1)-(J1) having the structures as shown in the following table:

-continued

| No. | Structure |
|---|---|
| (E) | [structure: 3,3-dimethyl-2,4-dihydroxybutanamide linked via NH-CH(CH3)-CH2-NH to 3-fluorobenzamide] |
| (E1) | [structure: (S)-3,3-dimethyl-2,4-dihydroxybutanamide linked via NH to (S)-α-methyl-CH2-NH to 3-fluorobenzamide] |
| (F) | [structure: 3,3-dimethyl-2,4-dihydroxybutanamide linked to 3-chlorobenzamide via ethylenediamine] |
| (F1) | [structure: (S)-3,3-dimethyl-2,4-dihydroxybutanamide linked to 3-chlorobenzamide, (S)-methyl] |
| (G) | [structure: 3,3-dimethyl-2,4-dihydroxybutanamide linked to 3-chloro-4-fluorobenzamide] |
| (G1) | [structure: (S)- configuration, 3,3-dimethyl-2,4-dihydroxybutanamide to 3-chloro-4-fluorobenzamide] |
| (H) | [structure: 3,3-dimethyl-2,4-dihydroxybutanamide linked to 3,4-difluorobenzamide] |

-continued

| No. | Structure |
|---|---|
| (H1) | [structure: (S)- 3,3-dimethyl-2,4-dihydroxybutanamide linked to 3,4-difluorobenzamide, (S)-methyl] |
| (I) | [structure: 3,3-dimethyl-2,4-dihydroxybutanamide to 5-chloro-2-fluorobenzamide] |
| (I1) | [structure: (S)- configuration to 5-chloro-2-fluorobenzamide] |
| (J) | [structure: 3,3-dimethyl-2,4-dihydroxybutanamide to 2,5-difluorobenzamide] |
| (J1) | [structure: (S)- configuration to 2,5-difluorobenzamide] |

7. The compound according to claim 6, selected from the compounds (A1), (B1), (C1) and (E1).

8. The compound according to claim 7, wherein the compound is (A1).

9. A pharmaceutical composition comprising an anti-malarial compound as defined in claim 1 and a pharmaceutically acceptable excipient.

10. The pharmaceutical composition according to claim 9, said composition comprising an additional anti-malarial agent.

11. The pharmaceutical composition according to claim 10, wherein said additional anti-malarial agent is selected from the groups consisting of atovaquone, chloroquine, hydroxychloroquine, primaquine, proguanil, quinidine, quinine, quinacrine, pyrimethamine-sulfadoxine, halofantrine, mefloquine, doxycycline, lumefantrine, amodiaquine, piperaquine, ferroquine, tafenoquine, arterolane, pyronaridine, artemisinin, artesunate, artemether, dihydroartemisinin, artenimol, Spiro[3H-indole-3,1'-[1H]pyrido[3,4-b]indol]-2 (1H)-one, 5,7'-dichloro-6'-fluoro-2',3',4',9'-tetrahydro-3'-methyl-,(1'R,3'S)-(CAS Registry Number: 1193314-23-6), Sulfur, [4-[[2-(1,1-difluoroethyl)-5-methyl[1,2,4]triazolo[1, 5-a]pyrimidin-7-yl]amino]phenyl]pentafluoro-] (CAS Registry Number: 1282041-94-4), Morpholine,4-[2-(4-cis-dispiro [cyclohexane-1,3'-[1,2,4]trioxolane-5',2"-tricyclo [3.3.1.1$^{3,7}$]-decan]-4-ylphenoxy)ethyl]-(CAS Registry Number: 1029939-86-3), [3,3'-Bipyridin]-2-amine, 5-[4-(methylsulfonyl)phenyl]-6'-(trifluoromethyl)-(CAS Registry Number: 1314883-11-8), and Ethanone, 2-amino-1-[2-(4-fluorophenyl)-3-[(4-fluorophenyl)amino]-5,6-dihydroimidazo [1,2-a]pyrazin-7(8H)-yl]-(CAS Registry Number: 1261109-90-3).

* * * * *